US008058255B2

(12) United States Patent
Ford et al.

(10) Patent No.: US 8,058,255 B2
(45) Date of Patent: Nov. 15, 2011

(54) METHODS AND COMPOSITIONS CONCERNING SIRNA'S AS MEDIATORS OF RNA INTERFERENCE

(75) Inventors: Lance P. Ford, Austin, TX (US); Joseph Krebs, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 12/484,948

(22) Filed: Jun. 15, 2009

(65) Prior Publication Data

US 2010/0159591 A1     Jun. 24, 2010

Related U.S. Application Data

(63) Continuation of application No. 11/020,560, filed on Dec. 23, 2004, now abandoned.

(51) Int. Cl.
 *A01N 43/04* (2006.01)
 *A61K 31/70* (2006.01)
(52) U.S. Cl. .................................................. 514/44 A
(58) Field of Classification Search ................. 514/44 A
 See application file for complete search history.

(56) References Cited

U.S. PATENT DOCUMENTS

| 4,415,732 A | 11/1983 | Caruthers et al. ................ 536/27 |
| 4,458,066 A | 7/1984 | Caruthers et al. ................ 536/27 |
| 4,683,202 A | 7/1987 | Mullis .............................. 435/91 |
| 4,786,600 A | 11/1988 | Kramer et al. ................. 435/235 |
| 4,828,979 A | 5/1989 | Kievan et al. ...................... 435/6 |
| 4,849,513 A | 7/1989 | Smith et al. ....................... 536/27 |
| 4,910,300 A | 3/1990 | Urdea et al. ................... 536/287 |
| 4,952,496 A | 8/1990 | Studier et al. .................... 435/91 |
| 5,026,645 A | 6/1991 | Kotani et al. ................... 435/194 |
| 5,037,735 A | 8/1991 | Khanna et al. ................ 435/7.6 |
| 5,102,802 A | 4/1992 | McAllister ............... 435/252.33 |
| 5,241,060 A | 8/1993 | Engelhardt et al. ............ 536/27 |
| 5,489,527 A | 2/1996 | Wilson ....................... 435/240.1 |
| 5,573,913 A | 11/1996 | Rosemeyer et al. .............. 435/6 |
| 5,591,601 A | 1/1997 | Wagner et al. ............... 435/69.1 |
| RE35,443 E | 2/1997 | DeFrancesco et al. ....... 435/194 |
| 5,624,803 A | 4/1997 | Noonberg et al. ................ 435/6 |
| 5,643,768 A | 7/1997 | Kawasaki ....................... 435/91 |
| 5,645,897 A | 7/1997 | Andra .......................... 427/526 |
| 5,705,629 A | 1/1998 | Bhongle .................... 536/25.34 |
| 5,728,525 A | 3/1998 | Conrad ............................. 435/6 |
| 5,734,039 A | 3/1998 | Calabretta ................... 536/24.5 |
| 5,776,905 A | 7/1998 | Gibbons et al. ................ 514/44 |
| 5,795,715 A | 8/1998 | Livache et al. .................... 435/6 |
| 5,824,528 A | 10/1998 | Studier et al. ................. 435/194 |
| 5,869,320 A | 2/1999 | Studier et al. ............ 435/252.33 |
| 5,889,136 A | 3/1999 | Scaringe et al. ........... 536/25.34 |
| 5,891,681 A | 4/1999 | Mallet et al. ................. 435/91.1 |
| 5,898,031 A | 4/1999 | Crooke ...................... 435/172.3 |
| 5,998,135 A | 12/1999 | Rabbani et al. .................... 435/6 |
| 5,998,203 A | 12/1999 | Matulic-Adamic et al. .. 435/325 |
| 6,005,087 A | 12/1999 | Cook et al. ................... 536/23.1 |
| 6,083,482 A | 7/2000 | Wang ............................ 424/1.73 |
| 6,107,094 A | 8/2000 | Crooke ......................... 424/1.73 |
| 6,114,152 A | 9/2000 | Serafini et al. ................ 435/91.2 |
| 6,262,252 B1 | 7/2001 | Wolff et al. ................. 536/25.32 |
| 6,268,490 B1 | 7/2001 | Imanishi et al. .............. 536/23.1 |
| 6,372,433 B1 | 4/2002 | Baker et al. ......................... 435/6 |
| 6,376,179 B1 | 4/2002 | Laayoun ............................ 435/6 |
| 6,455,292 B1 | 9/2002 | Shu et al. ....................... 435/194 |
| 6,506,559 B1 | 1/2003 | Fire et al. ............................ 435/6 |
| 6,525,191 B1 | 2/2003 | Ramasamy .................. 536/28.7 |
| 6,573,099 B2 | 6/2003 | Graham ......................... 435/455 |
| 6,639,059 B1 | 10/2003 | Kochkine et al. .............. 536/4.1 |
| 6,670,461 B1 | 12/2003 | Wengel et al. ................ 539/23.1 |
| 6,673,611 B2 | 1/2004 | Thompson et al. ........... 435/455 |
| 6,734,291 B2 | 5/2004 | Kochkine et al. .............. 536/4.1 |
| 6,770,748 B2 | 8/2004 | Imanishi et al. ............. 536/23.1 |
| 6,794,499 B2 | 9/2004 | Wengel et al. ............... 536/23.1 |
| 6,849,726 B2 | 2/2005 | Usman et al. ................ 536/23.1 |
| 7,022,828 B2 | 4/2006 | McSwiggen et al. ........ 536/23.1 |
| 7,034,133 B2 | 4/2006 | Wengel et al. ............... 536/23.1 |
| 7,053,207 B2 | 5/2006 | Wengel ......................... 536/25.3 |
| 7,056,704 B2 | 6/2006 | Tuschl et al. ................. 435/91.1 |
| 7,060,809 B2 | 6/2006 | Wengel et al. ............... 536/23.1 |
| 7,074,558 B2 | 7/2006 | Haydock et al. |
| 7,078,196 B2 | 7/2006 | Tuschl et al. ................. 435/91.1 |
| 7,084,125 B2 | 8/2006 | Wengel ............................ 514/44 |
| 7,176,304 B2 | 2/2007 | McSwiggen et al. ........ 536/24.5 |
| 7,790,878 B2 * | 9/2010 | Barik ............................ 536/24.5 |
| 2002/0086356 A1 | 7/2002 | Tuschl et al. ................. 435/69.1 |
| 2002/0162126 A1 | 10/2002 | Beach et al. ....................... 800/8 |
| 2002/0173478 A1 | 11/2002 | Gewirtz .......................... 514/44 |

(Continued)

FOREIGN PATENT DOCUMENTS

| EP | 0178863 | 10/1985 |
| EP | 0266032 | 8/1987 |
| WO | WO 88/10315 | 6/1988 |
| WO | WO 91/02818 | 3/1991 |
| WO | WO 91/05866 | 5/1991 |
| WO | WO 99/32619 | 12/1998 |
| WO | WO 00/01846 | 1/2000 |
| WO | WO 00/44914 | 8/2000 |
| WO | WO 01/68836 | 3/2001 |
| WO | WO 01/36646 | 5/2001 |
| WO | WO 01/75164 | 10/2001 |
| WO | WO 01/96584 | 12/2001 |
| WO | WO 02/44321 | 6/2002 |
| WO | WO 03/070918 | 8/2003 |
| WO | WO 03/100059 | 12/2003 |
| WO | WO 03/102214 | 12/2003 |
| WO | WO 03/106630 | 12/2003 |
| WO | WO 03/106631 | 12/2003 |
| WO | WO 2005/035004 | 4/2005 |

OTHER PUBLICATIONS

Kits for Labeling DNA, BioDirectory'98, Amersham Pharmacia Biotech, p. 136, 1998.

(Continued)

*Primary Examiner* — Brian Whiteman

(57) ABSTRACT

The present invention concerns an isolated siRNA of from about 5 to about 20 nucleotides that mediates RNA interference. Also disclosed are methods of reducing expression of a target gene in a cell comprising obtaining at least one siRNA of 5, 6, 7, 8, 9, 10, 11, 12, 13, 14, 15, 16, 17, 18, 19, or 20 basepairs in length; and delivering the siRNA into the cell. The siRNAs can be chemically synthesized RNA or an analog of a naturally occurring RNA.

19 Claims, 2 Drawing Sheets

U.S. PATENT DOCUMENTS

| | | | | |
|---|---|---|---|---|
| 2002/0197641 A1* | 12/2002 | Minc-Golomb | | 435/6 |
| 2003/0009295 A1 | 1/2003 | Markowitz et al. | | 702/20 |
| 2003/0044941 A1 | 3/2003 | Crooke | | 435/91.2 |
| 2003/0077609 A1 | 4/2003 | Jakobsen et al. | | 435/6 |
| 2003/0108923 A1 | 6/2003 | Tuschl et al. | | 435/6 |
| 2003/0119104 A1 | 6/2003 | Perkins et al. | | 435/69.1 |
| 2003/0153519 A1* | 8/2003 | Kay et al. | | 514/44 |
| 2003/0166282 A1 | 9/2003 | Brown et al. | | 435/455 |
| 2003/0203868 A1* | 10/2003 | Bushman et al. | | 514/44 |
| 2003/0224377 A1 | 12/2003 | Wengel et al. | | 435/6 |
| 2003/0224432 A1 | 12/2003 | Myers et al. | | 435/6 |
| 2004/0014108 A1 | 1/2004 | Eldrup et al. | | 435/6 |
| 2004/0029275 A1 | 2/2004 | Brown et al. | | 435/375 |
| 2004/0033602 A1 | 2/2004 | Ford et al. | | 435/455 |
| 2004/0038921 A1 | 2/2004 | Kreutzer et al. | | 514/44 |
| 2004/0053875 A1 | 3/2004 | Kreutzer et al. | | 514/44 |
| 2004/0067882 A1 | 4/2004 | Alsobrook, II et al. | | 53/33 |
| 2004/0072779 A1 | 4/2004 | Kreutzer et al. | | 514/44 |
| 2004/0091926 A1 | 5/2004 | Liu et al. | | 435/6 |
| 2004/0096843 A1 | 5/2004 | Rossi et al. | | 435/6 |
| 2004/0102408 A1 | 5/2004 | Kreutzer et al. | | 514/44 |
| 2004/0147022 A1 | 7/2004 | Baker et al. | | 435/375 |
| 2004/0171031 A1 | 9/2004 | Baker et al. | | 435/6 |
| 2004/0171033 A1 | 9/2004 | Baker et al. | | 435/6 |
| 2004/0171570 A1 | 9/2004 | Allerson et al. | | 514/44 |
| 2004/0175703 A1 | 9/2004 | Kreutzer et al. | | 514/44 |
| 2004/0198640 A1 | 10/2004 | Leake et al. | | 514/8 |
| 2004/0203024 A1 | 10/2004 | Baker et al. | | 435/6 |
| 2004/0203145 A1 | 10/2004 | Zamore et al. | | 435/375 |
| 2004/0219565 A1 | 11/2004 | Kauppinen et al. | | 435/6 |
| 2004/0229266 A1 | 11/2004 | Tuschl et al. | | 435/6 |
| 2004/0248094 A1 | 12/2004 | Ford et al. | | 435/6 |
| 2004/0248299 A1 | 12/2004 | Jayasena et al. | | 435/455 |
| 2004/0259097 A1 | 12/2004 | De Backer et al. | | 435/6 |
| 2004/0259247 A1 | 12/2004 | Tuschl et al. | | 435/375 |
| 2005/0020521 A1 | 1/2005 | Rana | | 514/44 |
| 2005/0020525 A1 | 1/2005 | McSwiggen et al. | | 514/44 |
| 2005/0026160 A1 | 2/2005 | Allerson et al. | | 435/6 |
| 2005/0058982 A1 | 3/2005 | Han et al. | | 435/5 |
| 2005/0080246 A1 | 4/2005 | Allerson et al. | | 536/23 |
| 2005/0100907 A1 | 5/2005 | Kreutzer et al. | | 514/23.1 |
| 2005/0119214 A1 | 6/2005 | Manoharan et al. | | 514/44 |
| 2005/0176018 A1 | 8/2005 | Thompson et al. | | 435/6 |
| 2005/0214823 A1 | 9/2005 | Blume et al. | | 435/6 |
| 2005/0223427 A1 | 10/2005 | Leake et al. | | 800/286 |
| 2005/0244858 A1 | 11/2005 | Rossi et al. | | 435/6 |
| 2005/0256071 A1 | 11/2005 | Davis | | 514/44 |
| 2005/0287566 A1 | 12/2005 | Wengel | | 435/6 |
| 2006/0134787 A1 | 6/2006 | Zamore et al. | | 435/455 |
| 2006/0142228 A1 | 6/2006 | Ford et al. | | 514/44 |
| 2006/0166910 A1 | 7/2006 | Tuschl et al. | | 514/44 |
| 2006/0217334 A1 | 9/2006 | McSwiggen et al. | | 514/44 |
| 2006/0217335 A1 | 9/2006 | McSwiggen et al. | | 514/44 |
| 2006/0217336 A1 | 9/2006 | McSwiggen et al. | | 514/44 |
| 2006/0217337 A1 | 9/2006 | McSwiggen et al. | | 514/44 |
| 2006/0247428 A1 | 11/2006 | McSwiggen et al. | | 536/23.1 |
| 2006/0247429 A1 | 11/2006 | McSwiggen et al. | | 536/23.1 |
| 2006/0276635 A1 | 12/2006 | McSwiggen et al. | | 536/44 |
| 2006/0287266 A1 | 12/2006 | McSwiggen et al. | | 514/44 |
| 2006/0293271 A1 | 12/2006 | McSwiggen et al. | | 514/44 |
| 2007/0004663 A1 | 1/2007 | McSwiggen et al. | | 514/44 |
| 2007/0004665 A1 | 1/2007 | McSwiggen et al. | | 514/44 |
| 2007/0004667 A1 | 1/2007 | McSwiggen et al. | | 514/44 |
| 2007/0111228 A1 | 5/2007 | Jayasena et al. | | 435/6 |
| 2007/0265438 A1 | 11/2007 | Khvorova et al. | | 536/24.1 |
| 2008/0086002 A1 | 4/2008 | Khvorova et al. | | 536/24.5 |

OTHER PUBLICATIONS

OligofectAMINE Reagent product information, Cat. No. 12252-01 Invitrogen Life Reagent, Reviewed Aug. 23, 2001.

Amarzguioui et al., "Tolerance for Mutations and Chemical Modification in a siRNA," *Nucleic Acids Research*, 31(2):589-595, 2003.

Ambion Inc., "RNA Interference and Gene Silencing—an Update," printed from http://www.ambion.com/hottopics/RNAi/rnai_jun2001.html, Jun. 2001.

Ambion Inc., "Products for RNA Structure/Function Analysis," *Ambion TechNotes*, 8(5):1-3, Nov. 2001.

Ambion Inc., "*Silencer*™ siRNA Construction Kit—Protocol—Large Scale Synthesis and Purification of siRNAs," Catalog #1620, Sep. 2002.

Ambion Inc., "Design and testing of siRNAs," *Ambion TechNotes*, 9(1):4, Feb. 2002.

Ambion Inc., "RNA Interface in Mammalian Cell Culture: Design, Execution and Anaysis of the siRNA Effect," *Ambion TechNotes*, 9(1):1-6, Feb. 2002.

Ambion Inc., *Ambion TechNotes*, 9(3):1-19, Jun. 2002.

Ambion Inc., *Ambion TechNotes*, a newsletter from 9(4), 2002.

Ambion Inc., "High sensitivity qRT-PCR—MessageSensor™ reverse transcription kit for one step qRT-PCR," *Ambion TechNotes Newsletter*, 10(1):1-19 (entire newsletter), 2003.

Ambion Inc., "Enhanced siRNA Delivery and Long-Term Gene Silencing," *Ambion TechNotes Newsletter*, 12(1):22-25, 2003.

Ambion Inc., "The Best Controls for siRNA Experiments—Now Available with More Choices," *Ambion TechNotes Newsletter*, 12(1):22-25, 2003.

siRNA target finder for GenBnak Accession No. AF007834, Ambion siRNA Target Finder, Austin, TX, Ambion, Jun. 2002: [retrieved on Oct. 18, 2007]. Retrieved from the internet: http://www.ambion.com/.

Anonymous, "The siRNA user guide." Revised Aug. 26, 2001, [online], [retrieved on Jan. 31, 2002] Retrieved from Max Planck Institute for Biophysical Chemistry using Internet <URL:http://www.mpibpc.gwdg.de/abteilungen/100/105/siRNAuserguide.pdf>.

Atschul et al., "Basic local alignment search tool," *J. Molec. Biol.*, 215:403-410, 1990.

Baglioni and Nilson, "Mechanisms of antiviral action of interferon," *Interferon*, 5:23-42, 1983.

Bergstrom et al., "Comparison of the base pairing properties of a series of nitroazole nucleobase analogs in the oligodeoxyribonucleiotide sequence 5'-d(CGCXAATTYGCG)-3'," *Nucleic Acids Res.* 25(10):1935-1942, 1997.

Bernstein et al., "Role for a bidentate ribonuclease in the initiation step of RNA interference," *Nature*, 409: 363-366—Supplement 1-8, 2001.

Black et al. "Studies on the toxicity and antiviral activity of various polynucleotides," *Antimicrob. Agents Chemotherap.*, 3(2):198-206, 1972.

Blaszczyk et al., "Crystallographic and modeling studies of RNase III suggest a mechanism for double-stranded RNA cleavage," *Structure*, 9(12):1225-1236, 2001.

Bosher et al., "RNA interference: genetic wand and genetic watchdog," *Nat. Cell. Biol.*, 2:E31-E36, 2000.

Brummelkamp et al., "A system for stable expression of short interfering RNAs in mammalian cells," *Science*, 296(5567):550-553, 2002.

Byrom et al., "Inducing RNAi with siRNA cocktails generated by RNAse III," *Ambion TechNotes Newsletter*, 10(1):4-6, 2003.

Caplen et al., "Specific inhibition of gene expression by small double-stranded RNAs in invertebrate and vertebrate systems," *Proc Natl Acad Sci USA*, 98(17):9742-9747, 2001.

Catalanotto et al., "Transcription: gene silencing in worms and fungi," *Nature*, 404(6775):245, 2000.

Chiu et al., "RNAi in Human Cells: Basic Structural and Functional Features of Small Interfering RNA," *Molecular Cell*, vol. 10, pp. 549-561, Sep. 2002.

Chiu et al., "siRNA Function in RNAi: A Chemical Modification Analysis," *RNA*, 9:1034-1048, 2003.

Cogoni and Macino, "Gene silencing in *Neurospora crassa* requires a protein homologous to RNA-dependent RNA polymerase," *Nature*, 399:166-169, 1999.

Cogoni and Macino, "Posttranscriptional gene silencing in *Neurospora* by a RecQ DNA helicase," *Science*, 286:2342-2344, 1999.

Cormack et al., "Cloning of PCR products using the green floorscent protein", United States National Library of Medicine, Accession No. AF007834; 1997.

Cummins et al., "Characterization of fully 2'—Modified Oligoribonucleotide Hetero- and Homoduplex Hybridization and Nuclease Sensitivity," *Nucleic Acids Research*, 23(11):2019-2024, 1995.

Czauderna et al., "Structural Variations and Stabilising Modifications of Synthetic siRNAs in Mammalian Cells," *Nucleic Acids Research*, 31(11):2705-2716, 2003.

Dalmay et al., "An RNA-dependent RNA polymerase gene in *Arabidopsis* is required for posttranscriptional gene silencing mediated by a transgene but not by a virus," *Cell*, 101:543-553, 2000.

Dalmay et al., "SDE3 encodes an RNA helicase required for posttranscriptional gene silencing in *Arabidopsis*," *EMBO J.*, 20(8):2069-2078, 2001.

Devereux et al., "A comprehensive set of sequence analysis programs for the VAC," *Nucleic Acid. Res.*, 12(1):387-395, 1984.

Dewanjee et al., "Kinetics of Hybridization of mRNA of *c-myc* Oncogene with 111 in Labeled Antisense Oligodeoxynucleotide Probes by High-Pressure Liquid Chromatography," *Biotechniques*, 16(5):844-850, 1994.

Dharmacon Research. (Jul. 2001) siRNA Oligonucleotides for RNAi Applications: Dharmacon siACE-RNAi™ Options. Technical Bulletin #003. [online], [retrieved on Jan. 31, 2002] using Internet http://www.dharmacon.com/tech/tech003.html>.

Dharmacon Research. (Aug. 2001) siRNA Oligonucleotides for RNAi Applications: Dharmacon siACE-RNAi™ Options. Technical Bulletin #003—Revision A [online], [retrieved on Jan. 31, 2002] using Internet http://www.dharmacon.com/tech/tech003.html, 12 pages.

Dias et al., "Antisense Oligonucleotides: Basic Concepts and Mechanisms," *Molecular Cancer Therapeutics*, vol. 1:347-355, Mar. 2002.

Diaz et al., "Hierarchy of base-pair preference in the binding domain of the bacteriophage T7 promoter," *J. Mol. Biol.*, 229:805-811, 1993.

Donzé and Picard, "RNA interference in mammalian cells using siRNAs synthesized with T7 RNA polymerase," *Nucleic Acids Research*, 30(10):e46:1-4, 2002.

Downward, "RNA Interference," BMJ, vol. 328, pp. 1245-1248, May 22, 2004.

Dubins et al., "On the stability of double stranded nucleic acids," *J. Am. Chem. Soc.*, 123:9254-9259, 2001.

Elbashir et al., "Analysis of gene function in somatic mammalian cells using small interfering RNAs," *Methods*, 26:199-213, 2002.

Elbashir et al., "Duplexes of 21-nucleotide RNAs mediate RNA interference in cultured mammalian cells," *Nature*, 411:494-498, 2001.

Elbashir et al., "Functional anatomy of siRNAs for mediating efficient RNAi in *Drosphila melanogaster* embryo lysate," *EMBO J*, 20(23):6877-6888, 2001.

Elbashir et al., "RNA interference is mediated by 21-and 22-nucleotide RNAs," *Genes & Development*, 15:188-200, 2001.

Feature of the week—RNA interference, *Nature*, Mar. 16, 2000.

Fire et al., "Potent and specific genetic interference by double-stranded RNA in *Caenorhabditis elegans*," *Nature*, 391:806-811, 1998.

Ford and Latham, "RNAi and Microarrays Reveal Biological Pathways: The combination of RNAi with microarrays has enormous potential for elucidating biological pathways. However, before this potential can be fulfilled, important questions need to be answered to ensure the proper interpretation of gene silencing results," *R&D Magazine*, Jul. 2003. pp. 48 (3 pages).

Froehler, et al. "Synthesis of DNA via deoxynucleoside H-phosphonate intermediates," *Nucleic Acids Res.*, 14(13):5399-5407, 1986.

Fuerst et al., "Use of hybrid vaccinia virus-T7 RNA polymerase system for expression of target genes," *Molecular and Cellular Biology*, 7(7):2538-2544, 1987.

Grishok et al., "Genes and mechanisms related to RNA interference regulate expression of the small temporal RNAs that control *C. elegans* developmental timing," *Cell*, 106:23-34, 2001.

Grishok et al., "Genetic Requirements for Inheritance of RNAi in *C. elegans*," *Science*, vol. 287:2494-2497, Mar. 31, 2000.

Grünweller et al., "Comparison of Different Antisense Strategies in Mammalian Cells Using Locked Nucleic Acids, 2'-O-methyl RNA, Phosphorothioates and small interfering RNA," *Nucleic Acids Research*, 31(12):3185-3193, 2003.

Hamilton and Baulcombe, "A species of small antisense RNA in posttranscriptional gene silencing in plants," *Science*, 286:950-952, 1999.

Hammond et al., "An RNA-directed nuclease mediates post-transcriptional gene silencing in *Drosophila* cells," *Nature*, 404(6775):293-296, 2000.

Hammond et al., "Argonaute2, a link between genetic and biochemical analyses of RNAi," *Science*, 293:1146-1150, 2001.

Hammond et al., "Post-transcriptional gene silencing by double-stranded RNA," *Nat. Rev. Genet.*, 2(2):110-119, 2001.

Hammond, "RNAi Technologies in *Drosophila* Cell Culture," *RNAi—A Guide to Gene Silencing*, (Cold Spring Harbor Laboratory Press, Hannon, Ed.) Chapter 16, pp. 345-360, 2003.

Han and Dervan, "Sequence-specific recognition of double helical RNA and RNA-DNA by triple helix formation," *Proc. Natl. Acad. Sci., USA*, 90:3806-3810, 1993.

Hannon et al., "Unlocking the Potential of the Human Genome with RNA Interference," *Nature* 431:371-378, 2004.

Harborth et al., "Identification of Essential Genes in Cultured Mammalian Cells Using Small Interfering RNAs," *Journal of Cell Science*, 114(24):4557-4565, 2001.

Hebert et al., "Purification of ribonucleases Sa, Sa2, and Sa3 after expression in *Escherichia coli*," *Protein Expr. Purif.*,11(2):162-168, 1997.

Higgins et al., "Clustal V: improved software for multiple sequence alignment," *Computer Applications in the Biosciences (CABIOS)*, 8(2):189-191, 1992.

Holen et al., Positional Effects of Short Interfering RNAs targeting the Human Coagulation Trigger Tissue Factor, *Nucleic Acids Research*, 30(8):1757-1766, 2002.

Holen, et al., "Similar behaviour of single-strand and double-strand siRNAs suggests they act through a common RNAi pathway," *Nucleic Acids Research*, 31(9):2401-2407, 2003.

Hough et al., "Why RNAi Makes Sense," *Nature Biotechnology*, vol. 21(7):731-732, Jul. 2003.

Hutvagner et al., "A cellular function for the RNA-interference enzyme Dicer in the maturation of the let-7 small temporal RNA," *Science*, 293:834-838, 2001.

Iyer et al., "3H-1,2-benzodithiole-3-one 1,1-dioxide as an improved sulfurizing reagent in the solid-phase synthesis of oligodeoxyribonucleoside phosphorothioates," *J. Am. Chem. Soc.*, 112:1253-1254, 1990.

Jackson et al., "Expression Profiling Reveals Off-Target Gene Regulation by RNAi," *Nature Biotechnology*, 21(6):635-638, Jun. 2003.

Jacque et al., "Modulation of HIV-1 replication by RNA interference," *Nature*, 418:435-438, 2002.

Kawase et al., "Studies on nucleic acid interactions I. Stabilities of mini-duplexes (dG2A4XA4G2-dC2T4YT4C2) and self-complementary d(GGAAXYTTCCC) containing deoxyinosine and other mismatched bases," *Nucleic Acids Res.*, 14(19):7727-7736, 1986.

Kennerdell et al., "Heritable Gene Silencing in *Drosophila* using Double-Stranded RNA," Nature Biotechnology 17:896-898, 2000.

Ketting and Plasterk, "A genetic link between co-suppression and RNA interference in *C. elegans*," *Nature*, 404(6775):296-298, 2000.

Ketting et al., "mut-7 of *C. elegans*, required for transposon silencing and RNA interference, is a homolog of Werner syndrome helicase and RNaseD," *Cell*, 99:133-141, 1999.

Kharrat et al., "Structure of the dsRNA binding domain of *E. coli* RNase III," *The EMBO. J.*, 14(14):3572-3584, 1995.

Kievits et al., "NASBAtm isothermal enzymatic in vitro nucleic acid amplification optimized for the diagnosis of HIV-1 infection," *Journal of Virological Methods*, 35:273-286, 1991.

Kimura et al., "Alterations of c-myc expression by antisense oligodeoxynucleotides enhance the induction of apoptosis in HL-60 cells," *Cancer Research*, 55:1379-1384, 1995.

Kita et al., "Modulation of polyglutamine-induced cell death by genes identified by expression profiling," *Human Molecular Genetics*, 11(19):2279-2287, 2002.

Knight and Bass, "A Role for the RNase III Enzyme DCR-1 in RNA Interference and Germ Line Development in *C. elegans*," *Science*, 293(5538):2269-2271, 2001.

Kuhnast et al., "General method to label antisense oligonucleotides with radioactive halogens for pharmacological and imaging studies," *Bioconjug. Chem.*, 11(5):627-636, 2000.

Kurreck, "Antisense Technologies: Improvement Through Novel Chemical Modifications," *Eur. J. Biochem*, 270:1628-1644, 2003.

Kuwasaki et al., "Hairpin Antisense Olignucleotides Containing 2'—Methoxynucleosides with Base-Pairing in the Stem Region at the 3'—end Penetration, Localization, and Anti-HIV Activity," *Biochemical Biophysical Res. Comm.*, 228:623-631, 1996.

Kuznicki et al., "Combinatorial RNA Interference Indicates GLH-4 Can Compensate for GLH-1; these two P Granule Components are Critical for Fertility in *C. elegans*," *Development*, 127:2907-2916, 2000.

Kwoh et al., "Transcription-based amplification system and detection of amplified human immunodeficiency virus type 1 with a bead-based sandwich hybridization format," *Proc. Natl. Acad. Sci. USA*, 86:1173-1177, 1989.

Latham et al., "Six Methods of inducing RNAI in Mammalian Cells," *RNA Interference Technology*, (Cambridge, Appasani, ed.,) pp. 147-160, 2005.

Lee et al., "Expression of small interfering RNAs targeted against HIV-1 rev transcripts in human cells," *Nat. Biotechnol.*, 19:500-505, 2002.

Lee et al., "Tissue-specific promoter usage in the $D_{1A}$ dopamine receptor gene in brain and kidney," *DNA and Cell Biol.*, 16(11):1267-1275, 1997.

Lesk, ed., Computational Molecular Biology. Oxford University Press, New York, 1988.

Li et al., "Double-stranded RNA injection produces null phenotypes in Zebrafish," *Developmental Biology*, 217:394-405, 2000.

Lin and Avery, "Policing rogue genes," *Nature*, 402:128-129, 2000.

Liu et al., "A scintillation proximity assay for rna detection," *Anal. Biochem.*, 289:239-245, 2001.

Lorenz et al., "Phosphorothioate Antisense Olignucleotides Induce the Formation of Nuclear Bodies," *Molecular Biology of the Cell*, vol. 9 1007-1023, May 1998.

Lu et al., "Delivering siRNA in vivo for Functional Genomics and Novel Therapeutics," *RNA Interference Technology*, (Cambridge, Appasani, ed.,) pp. 303-317, 2005.

Makeyev and Bamford, "Replicase activity of purified recombinant protein P2 of double-stranded RNA bacteriophage phi6," *EMBO J*, 19(1):124-133, 2001.

Manche, et al., "Interactions between Double-Stranded RNA Regulations and the Protein Kinase DAI", Molecular and Cellular Biology, 12:5238-5248, 1992.

Martinez et al., "Single-stranded antisense siRNAs guide target RNA cleavage in RNAi," *Cell*, 110(5):563-574, 2002.

McCaffrey et al., "RNA Interference in Adult Mice," *Nature*, vol. 418:38-39, Jul. 4, 2002.

McManus and Sharp, "Gene silencing in mammals by small interfering RNAs," *Nature Reviews, Genetics*, 3:737-747, 2002.

Meister et al., "Mechanisms of Gene Silencing by Double-Stranded RNA," *Nature* 431:343-349, 2004.

Milligan et al., Oligoribonucleotide synthesis using T7 RNA polymerase and synthetic DNA templates, *Nucleic Acids Res.* 25:8783-8798, 1987.

Miyagishi and Taira, "U6 promoter-driven siRNAs with four uridine 3' overhangs efficiently suppress targeted gene expression in mammalian cells," *Nat. Biotechnol.*, 5:497-500, 2002.

Montgomery et al., "RNA as a target of double-stranded RNA-mediated genetic interference in *Caenorhabditis elegans*," *Proc Natl Acad Sci USA*, 95:15502-15507, 1998.

Morgan et al., "A More Efficient and Specific Strategy in the Ablation of mRNA in *Xenopus laevis* Mixtures of Antisense Oligos," Nucleic Acids Research, vol. 21, No. 19:4615-4620, 1993.

Mourrain et al., "*Arabidopsis* SGS2 and SGS3 genes are required for posttranscriptional gene silencing and natural virus resistance," *Cell*, 101:533-542, 2000.

Myers et al. "Recombinant Dicer efficiently converts large dsRNAs into siRNAs suitable for gene silencing," *Nature Biotechnology*, 21:324-328, 2003.

Ngô et al., "Double-stranded RNA induces mRNA degradation in *Trypanosoma brucei*," *Proc. Natl. Acad. Sci., USA*, 95:14687-14692, 1998.

Nguyen et al., "Modification of DNA duplexes to smooth their thermal stability independently of their base content for DNA sequencing by hybridization," *Nucl. Acids Res.*, 25(15):3059-3065, 1997.

Novina et al., "siRNA-directed inhibition of HIV-1 infection," *Nat. Med.*, 8:681-686, 2002.

Nykanen et al., "ATP requirements and small interfering RNA structure in the RNA interference pathway," *Cell*, 107(3):309-321, 2001.

Oates et al., "Too Much Interference: Injection of Double-Stranded RNA has Nonspecific Effects in the Zebrafish Embryo," *Developmental Biology*, 224:20-28, 2000.

Pace et al., "Conformational stability and thermodynamics of folding of ribonucleases Sa, Sa2, and Sa3," *J. Mol. Biol.*, 279:271-286, 1998.

Paddison et al., "Short hairpin RNAs (shRNAs) induce sequence-specific silencing in mammalian cells," *Genes and Development*, 16:948-958, 2002.

Paddison et al., "Stable Suppression of Gene Expression by RNAI in Mammalian Cells," PNAS, 99(3):1443-1448, 2002.

Parrish et al., "Functional anatomy of a dsRNA trigger: differential requirement for two trigger strands in RNA interference," *Mol. Cell*, 6:1077-1087, 2000.

Paroo et al., "Challenges for RNAi in vivo," TRENDS in Biotechnology, vol. 22(8):390-394, Aug. 2004.

Paul et al., "Effective expression of small interfering RNA in human cells," *Nat. Biotechnol.*, 20:505-508, 2002.

Perkel, "Off-Target Effects Plague *Drosphila* RNAi," *The Scientist* pp. 1-5, 2006.

Plasterk and Ketting, "The silence of the genes," *Curr. Opin. Genet. Dev.*, 10:562-567, 2000.

Rakoczy et al., "Targeted Delivery of an Antisense Olignucleotide in the Retina: Uptake, Disruption, Stability, and effect," *Antisence Nucleic Acid Drug Dev.*, 6(3):207-213, 1996.

Ramos et al., "RNA recognition by a Staufen double-stranded RNA-binding domain," *EMBO Journal*, 19(5):997-1009, 2000.

Regnier and Preat, "Localization of a FITC-labeled phosphorothioate oligodeoxynucleotide in the skin after topical delivery by iontophoresis and electroporation," *Phar. Res.*, 15(10):1596-1602, 1998.

Reynolds et al., "Rational siRNA Design for RNA Interference," *Nature Biotechnology*, vol. 22(3):326-330, Mar. 2004.

Rusckowski et al., "Biodistrubution and metabolism of a mixed backbone oligonucleotide (GEM 231) following single and multiple dose administration in mice," *Antisense Nucleic Acid Drug Dev.*, 5:333-345, 2000.

Ruvkun, et al., "Glimpses of a Tiny RNA World", *Science*, 294:797-799, 2001.

Ryan and Birnie, "*Myc* oncogenes: the enigmatic family," *Biochem. J.*, 314:713-721, 1996.

Ryter and Schultz, "Molecular basis of double-stranded RNA-protein interactions: structure of a dsRNA-binding domain complexed with dsRNA," *EMBO J.*, 17:7505-7513, 1998.

Sambrook and Russell, *Molecular Cloning*, Cold Spring Harbor Laboratory Press, 2001.

Samarsky et al., "RNAi in Drug Development: Practical Considerations," *RNA Interference Technology*, (Cambridge, Appasani, ed.,) pp. 384-395, 2005.

Schmid et al., "Combinatoial RNAi: A Method for Evaluating the Function of Gene Families in *Drosophila*," TRENDS in Neurosciences, vol. 25, No. 2, Feb. 2002.

Sedelnikova et al., "Targeting the human mdr1 gene by 125I-labeled triplex-forming oligonucleotides," *Antisense Nucleic Acid Drug Dev.*, 10:443-452, 2000.

Sharp and Zamore, "RNA interference," *Science*, 287:2431-2433, 2000.

Sharp, "RNAi and double-strand RNA," *Genes Dev.*, 13:139-141, 1999.

Sharp, "RNA Interference-2001," Genes & Development, vol. 15, pp. 485-490, 2001.

Shishkina and Johnson, "A new method for the postsynthetic generation of abasic sites in oligomeric DNA," *Chem Res Toxicol*, 13:907-912, 2000.

Singh, et al., "Real Time Kinetics of Ribozyme Reactions," *Ribozyme Biochemistry and Biotechnology*, 351-371, A17-A20, 2000.

Smardon et al., "EGO-1 is related to RNA-directed RNA polymerase and functions in germ-line development and RNA interference in *C. elegans*," *Curr. Biol.*, 10:169-178, 2000.

Smith, ed. (1986) Biocomputing: Informatics and Genome Projects. Academic Press, New York, 1993.

St. Johnston et al., "A conserved double-stranded RNA-binding domain," *Proc. Natl. Acad. Sci., USA*, 89:10979-10983, 1992.

Stalnacke et al., "Radiotoxicity of 11C-methionine measured by the accumulation of DNA strand breaks in mammalian cells." *Eur. J. Nucl. Med.*, 11:166-170, 1985.

Stein, "The experimental use of antisense oligonucleotides: a guide for the perplexed," *J. Clinical Invest.*, 108(5): 641-644, 2001.

Sui et al., "A DNA vector-based RNAi technology to suppress gene expression in mammalian cells," *Proc. Natl. Acad. Sci. USA*, 99(8):5515-5520, 2002.

Svoboda et al., "RNAi Oocytes and Preimplantation Embryos: Effectiveness of Hairpin dsRNA," *Biochemical and Biophysical Research Communications*, 287:1099-1104, 2001.

Tabara et al., "The *rde-1* gene, RNA interference, and transposon silencing in *C. elegans*," *Cell*, 99:123-132, 1999.

Tavernarakis et al., "Heritable and Inducible Genetic Interference by Double-Stranded RNA encoded by Transgenes," *Nature Genetics* 24:180-183, 2000.

Testa et al., "Thermodynamics of RNA-RNA Duplexes with 2- or 4-thiouridines," *Biochemistry*, 38:16655-16662, 1999.

Thompson et al., "Clustal W: improving the sensitivity of progressive multiple sequence alignment through sequence weighting, position-specific gap penalties and weight matrix choice." *Nucleic Acids Res.* 22:4673-4680, 1994.

Timmons and Fire, "Specific interference by ingested dsRNA," *Nature*, 395:854, 1998.

Trotta et al., "BCR/ABL activates mdm2 mRNA translation via the La antigen," *Cancer Cell*, 3:145-160, 2003.

Tuschl et al., "Targeted mRNA degradation by double-stranded RNA in vitro," *Genes & Development*, 13:3191-3197, 1999.

Tuschl, "RNA interference and small interfering RNAs," *Chembiochem.*, 2:239-245, 2001.

Tuschl et al., "Small Interfering RNAs: A Revolutionary Tool for the Analysis of Gene Function and Gene Therapy," *Molecular Interventions*, vol. 2(3):158-167, Jun. 2002.

Vickers et al., "Efficient Reduction of Target RNAs by Small Interfering RNA and RNase H-dependant Antisense Agents," *The Journal of Biological Chemistry*, 278:7108-7118, 2003.

Vyas et al., "Ligand-receptor-mediated drug delivery: an emerging paradigm in cellular drug targeting," *Crit. Rev. Ther. Drug Carrier Syst.*, 18(1):1-76, 2001.

Waterhouse et al., "Gene silencing as an adaptive defence against viruses," *Nature*, 411:834-842, 2001.

Williams, "Gene expression domains as markers in developmental toxicity studies using mammalian embryo culture," *Int. J. Dev. Biol.*, 41(2):359-364, 1997.

Wincott et al., "Synthesis, Deprotection, analysis and Purification of RNA and Ribozymes," *Nucl. Acids Res.*, 23:2677-2684, 1995.

Wu et al., "Prevention of chain cleavage in the chemical synthesis of 2'-silylated oligoribonucleotides," *Nucl. Acids Res.*, 17(9):3501-3517, 1989.

Wu-Scharf et al., "Transgene and transposon silencing in *Chlamydomonas reinhardtii* by a DEAH-box RNA helicase," *Science*, 290:1159-1162, 2000.

Xia et al., "siRNA-mediated gene silencing in vitro and in vivo," *Nat. Biotechnol.*, 20(10):1006-1010, 2002.

Yang et al., "Short RNA duplexes produced by hydrolysis with *Escherichia coli* RNase III mediate effective RNA interference in mammalian cells," *Proc. Natl. Acad. Sci., USA*, 99(15):9942-9947, 2002.

Yoo, H, "Enhanced delivery of antisense oligonucleotides with fluorophore-conjugated PAMAM dendrimers," *Nucleic Acids Research*, 28:4225-4231, 2000.

Yu et al., "RNA interference by expression of short-interfering RNAs and hairpin RNAs in mammalian cells," *Proc. Natl. Acad. Sci., USA*, 99:6047-6052, 2002.

Zamore et al., "RNAi: double-stranded RNA directs the ATP-dependent cleavage of mRNA at 21 to 23 nucleotide intervals," *Cell*, 101: 25-33, 2000.

Zamore, "RNA interference: listening to the sound of silence," *Nat. Struct. Biol.*, 8:746-750, 2001.

Zhang et al., "Influence of different chelators (HYNIC, MAG3 and DTPA) on tumor cell accumulation and mouse biodistribution of technetium-99m labeled to antisense DNA," *Eur. J. Nucl. Med.*, 27(11):1700-1707, 2000.

Zhang et al., "Uptake and distribution of fluorescein-labeled D2 dopaminereceptor antisense oligdeoxynucleotide in mouse brain," *J. Mol. Neurosci.*, 7:13-28, 1996.

Zhang et al., "In vitro investigations of tumor targeting with 99mTc-labeled antisense DNA," *J. Nucl. Med.*, 42(11):1660-1669, 2001.

Zhao et al., "Double-Stranded RNA Injection Produces Nonspecific Defects in Zebrafish," *Developmental Biology*, 229:215-223, 2001.

EPO Search Report mailed Mar. 14, 2007 in App No. 03708928.1 entered into EP phase from PCT/US03/03023 entitled "High Potency siRNAS for Reducing the Expression of Target Genes;" Inventors: David Brown, Lance P. Ford, Rich Jarvis, Vince Pallotta, and Brittan Pasloske; Applicant: Ambion Inc.

PCT International Search Report with Written Opinion mailed Nov. 30, 2006 for PCT/US05/046779 filed Dec. 21, 2005 entitled "Methods and Compositions Concerning siRNAs as Mediators of RNA Interference;" Inventors: Brittan Pasloske, Lance P. Ford and Joseph Krebs; Applicant: Ambion Inc.

PCT International Search Report, for PCT/US03/03023, dated Jul. 18, 2005.

PCT International Search Report, for PCT/US03/18627, dated Mar. 16, 2004.

PCT International Search Report, for PCT/US03/18626, dated Feb. 11, 2004.

PCT International Search Report, for PCT/US03/36401, dated May 28, 2004.

USPTO issued Office Action mailed Nov. 29, 2005 in U.S. Appl. No. 10/355,820, filed Jan. 31, 2003 entitled "High Potency siRNAS for Reducing the Expression of Target Genes;" Inventors: David Brown, Lance P. Ford, Rich Jarvis, Vince Pallotta, and Brittan Pasloske; Assignee: Applera Corporation.

USPTO issued Final Office Action mailed May 30, 2006 in U.S. Appl. No. 10/355,820, filed Jan. 31, 2003 entitled "High Potency siRNAS for Reducing the Expression of Target Genes;" Inventors: David Brown, Lance P. Ford, Rich Jarvis, Vince Pallotta, and Brittan Pasloske; Assignee: Applera Corporation.

USPTO issued Office Action mailed Feb. 5, 2007 in U.S. Appl. No. 10/355,820, filed Jan. 31, 2003 entitled "High Potency siRNAS for Reducing the Expression of Target Genes;" Inventors: David Brown, Lance P. Ford, Rich Jarvis, Vince Pallotta, and Brittan Pasloske; Assignee: Applera Corporation.

EPO Communication pursuant to Article 96(2) EPC mailed Jun. 15, 2007 in App No. 03708928.1-2406 entered into EP phase from PCT/US03/03023 entitled "High Potency siRNAS for Reducing the Expression of Target Genes;" Inventors: David Brown, Lance P. Ford, Rich Jarvis, Vince Pallotta, & Brittan Pasloske; Applicant: Ambion Inc.

USPTO issued Office Action mailed Aug. 23, 2005 in U.S. Appl. No. 10/360,772, filed Jun. 12, 2002 entitled "Methods and Compositions Relating to Labeled RNA Molecules that Reduce Gene Expression;" Inventors: Lance P. Ford, Mike Byrom, & Brittan Pasloske; Assignee: Ambion Inc.

USPTO issued Final Office Action mailed May 16, 2006 in U.S. Appl. No. 10/360,772, filed Jun. 12, 2002 entitled "Methods and Compositions Relating to Labeled RNA Molecules that Reduce Gene Expression;" Inventors: Lance P. Ford, Mike Byrom, & Brittan Pasloske; Assignee: Ambion Inc.

USPTO issued Office Action mailed Oct. 30, 2006 in U.S. Appl. No. 10/360,772, filed Jun. 12, 2002 entitled "Methods and Compositions Relating to Labeled RNA Molecules that Reduce Gene Expression;" Inventors: Lance P. Ford, Mike Byrom, & Brittan Pasloske; Assignee: Ambion Inc.

USPTO issued Final Office Action mailed May 15, 2007 in U.S. Appl. No. 10/360,772, filed Jun. 12, 2002 entitled "Methods and Compositions Relating to Labeled RNA Molecules that Reduce Gene Expression;" Inventors: Lance P. Ford, Mike Byrom, & Brittan Pasloske; Assignee: Ambion Inc.

Written Opinion mailed Oct. 1, 2004 for PCT/US03/18627 filed Jun. 12, 2003 entitled "Methods and Compositions Relating to Labeled RNA Molecules that Reduce Gene Expression;" Inventors: Lance P. Ford, Mike Byrom, & Brittan Pasloske; Applicant: Ambion Inc.

Examination Report under Section 18(3) mailed May 27, 2005 for GB0500265.4, national phase of PCT/US03/18627 filed Jun. 12, 2003 entitled "Methods and Compositions Relating to Labeled RNA Molecules that Reduce Gene Expression;" Inventors: Lance P. Ford, Mike Byrom, & Brittan Pasloske; Applicant: Ambion Inc.

Examination Report under Section 18(3) mailed Nov. 29, 2005 for GB0500265.4, national phase of PCT/US03/18627 filed Jun. 12, 2003 entitled "Methods and Compositions Relating to Labeled RNA Molecules that Reduce Gene Expression;" Inventors: Lance P. Ford, Mike Byrom, & Brittan Pasloske; Applicant: Ambion Inc.

Examination Report under Section 18(3) mailed Jul. 28, 2006 for GB0500265.4, national phase of PCT/US03/18627 filed Jun. 12, 2003 entitled "Methods and Compositions Relating to Labeled RNA Molecules that Reduce Gene Expression;" Inventors: Lance P. Ford, Mike Byrom, & Brittan Pasloske; Applicant: Ambion Inc.

Certificate of Grant of Patent dated Nov. 1, 2006 for GB Patent No. 2406169; Appln. No. GB0500265.4, national phase of PCT/US03/18627 filed Jun. 12, 2003 entitled "Methods and Compositions Relating to Labeled RNA Molecules that Reduce Gene Expression;" Inventors: Lance P. Ford, Mike Byrom, & Brittan Pasloske; Applicant: Ambion Inc., Cover pages and granted claims.

USPTO issued Office Action mailed Apr. 25, 2006 in U.S. Appl. No. 10/460,775, filed Jun. 12, 2003 entitled "Methods and Compositions Relating to Polypeptides with RNase III Domains that mediate RNA Interference;" Inventors: Lance P. Ford, & David Brown; Assignee: Ambion Inc.

USPTO issued Office Action mailed Apr. 19, 2007 in U.S. Appl. No. 10/460,775, filed Jun. 12, 2003 entitled "Methods and Compositions Relating to Polypeptides with RNase III Domains that mediate RNA Interference;" Inventors: Lance P. Ford, & David Brown; Assignee: Ambion Inc.

Written Opinion mailed Sep. 23, 2004 for PCT/US03/18626 filed Nov. 12, 2003 entitled "Methods and Compositions Relating to Polypeptides with RNase III Domains that mediate RNA Interference;" Inventors: Lance P. Ford, & David Brown; Applicant: Ambion Inc.

EPO Communication pursuant to Article 96(2) EPC mailed Jan. 16, 2007 in App No. 03741956.1-2403 entered into EP phase from PCT/US03/18626 entitled "Methods and Compositions Relating to Polypeptides with RNase III Domains that mediate RNA Interference;" Inventors: Lance P. Ford, & David Brown; Applicant: Ambion Inc.

USPTO issued Office Action mailed Feb. 10, 2006 in U.S. Appl. No. 10/298,480, filed Nov. 15, 2002 entitled "Methods and Compositions for Reducing Target Gene Expression using Cocktails of siRNAs or Constructs Expressing siRNAs;" Inventors: David Brown, Lance P. Ford, & Rich Jarvis; Assignee: Ambion Inc.

USPTO issued Office Action mailed Oct. 10, 2006 in U.S. Appl. No. 10/298,480, filed Nov. 15, 2002 entitled "Methods and Compositions for Reducing Target Gene Expression using Cocktails of siRNAs or Constructs Expressing siRNAs;" Inventors: David Brown, Lance P. Ford, & Rich Jarvis; Assignee: Ambion Inc.

USPTO issued Final Office Action mailed May 30, 2007 in U.S. Appl. No. 10/298,480, filed Nov. 15, 2002 entitled "Methods and Compositions for Reducing Target Gene Expression using Cocktails of siRNAs or Constructs expressing siRNAs;" Inventors: David Brown, Lance P. Ford and Rich Jarvis; Assignee: Applera Corporation.

USPTO issued Office Action mailed Feb. 6, 2007 in U.S. Appl. No. 11/020,560, filed Dec. 23, 2004 entitled "Methods and Compositions Concerning siRNAs as Mediators of RNA Interference;" Inventors: Brittan Pasloske, Lance P. Ford and Joseph Krebs; Assignee: Applera Corporation.

USPTO issued Office Action mailed Sep. 18, 2007 in U.S. Appl. No. 10/355,820, filed Jan. 31, 2003 entitled "High Potency siRNAS for Reducing the Expression of Target Genes;" Inventors: David Brown, Lance P. Ford, Rich Jarvis, Vince Pallotta, and Brittan Pasloske; Assignee: Applera Corporation.

USPTO issued Office Action mailed Aug. 22, 2007 in U.S. Appl. No. 10/460,775, filed Jun. 12, 2003 entitled "Methods and Compositions Relating to Polypeptides with RNase III Domains that mediate RNA Interference;" Inventors: Lance P. Ford and David Brown; Assignee: Applera Corporation.

USPTO issued Final Office Action mailed Jan. 3, 2008 in U.S. Appl. No. 10/355,820, filed Jan. 31, 2003 "High Potency siRNAS for Reducing the Expression of Target Genes;" Inventors: David Brown, Lance P. Ford, Rich Jarvis, Vince Pallotta, and Brittan Pasloske; Assignee: Applera Corporation.

USPTO issued Final Office Action mailed Jan. 7, 2008 in U.S. Appl. No. 10/360,772, filed Jun. 12, 2002 entitled "Methods and Compositions Relating to Labeled RNA Molecules that Reduce Gene Expression;" Inventors: Lance P. Ford, Mike Byrom, & Brittan Pasloske; Assignee: Applera Corporation.

USPTO issued Office Action mailed Feb. 11, 2008 in U.S. Appl. No. 10/460,775, filed Jun. 12, 2003 entitled "Methods and Compositions Relating to Polypeptides with RNase III Domains that mediate RNA Interference;" Inventors: Lance P. Ford and David Brown; Assignee: Applera Corporation.

USPTO issued Final Office Action mailed Jan. 24, 2008 in U.S. Appl. No. 10/298,480, filed Nov. 15, 2002 entitled "Methods and Compositions for Reducing Target Gene Expression using Cocktails of siRNAs or Constructs expressing siRNAs;" Inventors: David Brown, Lance P. Ford and Rich Jarvis; Assignee: Applera Corporation.

USPTO issued Office Action mailed Dec. 7, 2007 in U.S. Appl. No. 11/020,560, filed Dec. 23, 2004 entitled "Methods and Compositions Concerning siRNAs as Mediators of RNA Interference;" Inventors: Brittan Pasloske, Lance P. Ford and Joseph Krebs; Assignee: Applera Corporation.

USPTO issued Office Action mailed Aug. 19, 2008 in U.S. Appl. No. 10/355,820, filed Jan. 31, 2003 "High Potency siRNAS for Reducing the Expression of Target Genes;" Inventors: David Brown, Lance P. Ford, Rich Jarvis, Vince Pallotta, and Brittan Pasloske; Assignee: Applera Corporation.

USPTO issued Final Office Action mailed Sep. 22, 2008 in U.S. Appl. No. 10/360,772, filed Jun. 12, 2002 entitled "Methods and Compositions Relating to Labeled RNA Molecules that Reduce Gene Expression;" Inventors: Lance P. Ford, Mike Byrom, & Brittan Pasloske; Assignee: Applera Corporation.

USPTO issued Office Action mailed Oct. 20, 2008 in U.S. Appl. No. 10/460,775, filed Jun. 12, 2003 entitled "Methods and Compositions Relating to Polypeptides with RNase III Domains that mediate RNA Interference;" Inventors: Lance P. Ford and David Brown; Assignee: Applera Corporation.

USPTO issued *Final* Office Action mailed Dec. 3, 2008 in U.S. Appl. No. 10/298,480, filed Nov. 15, 2002 entitled "Methods and Compositions for Reducing Target Gene Expression using Cocktails of siRNAs or Constructs expressing siRNAs;" Inventors: David Brown, Lance P. Ford and Rich Jarvis; Assignee: Applera Corporation.

USPTO issued Office Action mailed Aug. 5, 2008 in U.S. Appl. No. 11/020,560, filed Dec. 23, 2004 entitled "Methods and Compositions Concerning siRNAs as Mediators of RNA Interference;" Inventors: Brittan Pasloske, Lance P. Ford and Joseph Krebs; Assignee: Applera Corporation.

EPO Communication pursuant to Article 94(3) EPC mailed Jul. 15, 2008 in App No. 03741956.1-2403 entered into EP phase from PCT/US03/18626 entitled "Methods and Compositions Relating to Polypeptides with RNase III Domains that mediate RNA Interference;" Inventors: Lance P. Ford, & David Brown; Applicant: Ambion Inc.

USPTO issued Office Action mailed Mar. 31, 2009 in U.S. Appl. No. 10/355,820, filed Jan. 31, 2003 "High Potency siRNAS for Reducing the Expression of Target Genes;" Inventors: David Brown, Lance P. Ford, Rich Jarvis, Vince Pallotta, and Brittan Pasloske; Assignee: Applera Corporation.

USPTO issued Office Action mailed Apr. 28, 2009 in U.S. Appl. No. 10/360,772, filed Jun. 12, 2002 entitled "Methods and Compositions Relating to Labeled RNA Molecules that Reduce Gene Expression;" Inventors: Lance P. Ford, Mike Byrom, & Brittan Pasloske; Assignee: Applera Corporation.

USPTO issued Office Action mailed Apr. 16, 2009 in U.S. Appl. No. 10/460,775, filed Jun. 12, 2003 entitled "Methods and Compositions Relating to Polypeptides with RNase III Domains that mediate RNA Interference;" Inventors: Lance P. Ford and David Brown; Assignee: Applera Corporation.

USPTO issued Notice of Allowance mailed Mar. 16, 2009 in U.S. Appl. No. 11/020,560, filed Dec. 23, 2004 entitled "Methods and Compositions Concerning siRNAs as Mediators of RNA Interference;" Inventors: Brittan Pasloske, Lance P. Ford and Joseph Krebs; Assignee: Applera Corporation.

USPTO issued Final Office Action mailed Jul. 10, 2009 in U.S. Appl. No. 10/298,480, filed Nov. 15, 2002 entitled "Methods and Compositions for Reducing Target Gene Expression using Cocktails of siRNAs or Constructs expressing siRNAs;" Inventors: David Brown, Lance P. Ford and Rich Jarvis; Assignee: Applera Corporation.

Ambion Inc., "*Silencer*™ siRNA Labeling Kit—Instruction Manual," Catalog #1632, 1634, Jun. 2002.

* cited by examiner

METHODS AND COMPOSITIONS CONCERNING SIRNA'S AS MEDIATORS OF RNA INTERFERENCE

The present application is a continuation application of, and claims priority to U.S. patent application Ser. No. 11/020,560 filed Dec. 23, 2004, to Ford et al., now abandoned, which patent application is incorporated by reference herein in its entirety.

BACKGROUND OF THE INVENTION

1. Field of the Invention

The present invention relates generally to the field of molecular and cellular biology and has possible application for therapeutics. More particularly, it concerns the use of small interfering RNA's ("siRNA") as mediators of RNA interference ("RNAi").

2. Description of the Related Art

RNA interference, originally discovered in *Caenorhabditis elegans* by Fire and Mello (Fire et al., 1998), is a phenomenon in which double stranded RNA (dsRNA) reduces the expression of the gene to which the dsRNA corresponds. The phenomenon of RNAi was subsequently proven to exist in many organisms and to be a naturally occurring cellular process. The RNAi pathway can be used by the organism to inhibit viral infections, transposon jumping and to regulate the expression of endogenous genes (Huntvagner et al., 2001; Tuschl, 2001; Waterhouse et al., 2001; Zamore 2001). In original studies, researchers were inducing RNAi in non-mammalian systems and were using long double stranded RNAs. However, most mammalian cells have a potent anti-viral response causing global changes in gene expression patterns in response to long dsRNA thus arousing questions as to the existence of RNAi in humans. As more information about the mechanistic aspects of RNAi was gathered, RNAi in mammalian cells was shown to also exist.

In an in vitro system derived from *Drosophila* embryos, long dsRNAs are processed into shorter siRNA's by a cellular ribonuclease containing RNaseIII motifs (Bernstein et al., 2001; Grishok et al., 2001; Hamilton and Baulcombe, 1999; Knight and Bass, 2001; Zamore et al., 2000). Genetics studies done in *C. elegans, N. crassa* and *A. thaliana* have lead to the identification of additional components of the RNAi pathway. These genes include putative nucleases (Ketting et al., 1999), RNA-dependent RNA polymerases (Cogoni and Macino, 1999a; Dalmay et al., 2000; Mourrain et al., 2000; Smardon et al., 2000) and helicases (Cogoni and Macino, 1999b; Dalmay et al., 2001; Wu-Scharf et al., 2000). Several of these genes found in these functional screens are involved not only in RNAi but also in nonsense mediated mRNA decay, protection against transposon-transposition (Zamore, 2001), viral infection (Waterhouse et al., 2001), and embryonic development (Hutvagner et al., 2001; Knight and Bass, 2001). In general, it is thought that once the siRNAs are generated from longer dsRNAs in the cell by the RNaseIII like enzyme, the siRNA associate with a protein complex. The protein complex also called RNA-induced silencing complex (RISC), then guides the smaller 21 base double stranded siRNA to the mRNA where the two strands of the double stranded RNA separate, the antisense strand associates with the mRNA and a nuclease cleaves the mRNA at the site where the antisense strand of the siRNA binds (Hammond et al., 2001). The mRNA is then subsequently degraded by cellular nucleases.

Based upon some of the information mentioned above, Elbashir et al. (2001) discovered a method to bypass the anti viral response and induce gene specific silencing in mammalian cells. Several 21 nucleotide dsRNAs with 2 nucleotide 3' overhangs were transfected into mammalian cells without inducing a potent antiviral response. Their have been a few papers demonstrating that the siRNA can induce expression of some of the antiviral response genes at higher siRNA concentrations (Ford and Latham (2003)) The small dsRNA molecules (also referred to as "siRNA") were capable of inducing the specific suppression of target genes. In one set of experiments, siRNAs complementary to the luciferase gene were co-transfected with a luciferase reporter plasmid into NIH3T3, COS-7, HeLaS3, and 293 cells. In all cases, the siRNAs were able to specifically reduce luciferase gene expression. In addition, the authors demonstrated that siRNAs could reduce the expression of several endogenous genes in human cells. The endogenous targets were lamin A/C, lamin B1, nuclear mitotic apparatus protein, and vimentin. The use of siRNAs to modulate gene expression has now been reproduced by at least two other labs (Caplen et al., 2001; Hutvagner et al., 2001) and has been shown to exist in more that 10 different organisms spanning a large spectrum of the evolutionary tree.

The making of siRNAs has been through direct chemical synthesis, through processing of longer double stranded RNAs exposure to *Drosophila* embryo lysates, through an in vitro system derived from S2 cells, using page polymerase promoters, RNA-dependant RNA polymeras, and DNA based vectors. Use of cell lysates or in vitro processing may further involve the subsequent isolation of the short, 21-23 nucleotide siRNAs from the lysate, etc., making the process somewhat cumbersome and expensive. Chemical synthesis proceeds by making two single stranded RNA-oligomers followed by the annealing of the two single stranded oligomers into a double stranded RNA.

WO 99/32619 and WO 01/68836 suggest that RNA for use in siRNA may be chemically or enzymatically synthesized. The enzymatic synthesis contemplated is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25 mer lengths with the endogenous nuclease complex that converts long dsRNAs to siRNAs in vivo. They do not describe or present data for synthesizing and using in vitro transcribed 21-25 mer dsRNAs. No distinction is made between the expected properties of chemical or enzymatically synthesized dsRNA in its use in RNA interference.

Similarly, WO 00/44914 suggests that single strands of RNA can be produced enzymatically or by partial/total organic synthesis. Preferably, single stranded RNA is enzymatically synthesized from the PCR products of a DNA template, preferably a cloned cDNA template and the RNA product is a complete transcript of the cDNA, which may comprise hundreds of nucleotides. WO 01/36646 places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences. U.S. Pat. No. 5,795,715 was filed Jun. 17, 1994, well before the phenomenon of RNA interference was described by Fire, et al. (1998). The production of siRNA was therefore, not contemplated by these authors.

In the provisional patent 60/353,332, which is specifically incorporated by reference, the production of siRNA using the RNA dependent RNA polymerase, P2 and that this dsRNA can be used to induce gene silencing. Although this method is not commercially available or published in a scientific journal it was determined to be feasible. Several laboratories have demonstrated that DNA expression vectors containing mammalian RNA polymerase III promoters can drive the expression of siRNA that can induce gene-silencing (Brummelkamp et al., 2002; Sui et al., 2002; Lee et al., 2002; Yu et al., 2002; Miyagishi et al., 2002; Paul et al., 2002). The RNA produced from the polymerase III promoter can be designed such that it forms a predicted hairpin with a 19-base stem and a 3-8 base loop. The approximately 45 base long siRNA expressed as a single transcription unit folds back on it self to form the hairpin structure as described above. Hairpin RNA can enter the RNAi pathway and induce gene silencing. The siRNA mammalian expression vectors have also been used to express the sense and antisense strands of the siRNA under separate polymerase III promoters. In this case, the sense and antisense strands must hybridize in the cell following their transcription (Lee et al., 2002; Miyagishi et al., 2002). The siRNA produced from the mammalian expression vectors weather a hairpin or as separate sense and antisense strands were able to induce RNAi without inducing the antiviral response. More recent work described the use of the mammalian expression vectors to express siRNA that inhibit viral infection (Jacque et al., 2002; Lee et al., 2002; Novina et al., 2002). A single point mutation in the siRNA with respect to the target prevents the inhibition of viral infection that is observed with the wild type siRNA. This suggests that siRNA mammalian expression vectors and siRNA could be used to treat viral diseases.

An alternative enzymatic approach to siRNA production that elevates the need to perform screens for siRNA that are functional. Currently, a 4 or more siRNA to one target need to be designed to a single target. A siRNA synthesis method that would get around transfecting 4 or more separate siRNA per target would be beneficial in cost and time. Therefore, a method in which a mixture of siRNA can be made from a single reaction would increase the likely hood of knocking down the gene the first time it is performed. In order to generate this mixture of siRNA one approach would be using RNaseIII type nucleases. Recombinant bacterial RNaseIII (25.6 KDa) is one such nuclease that can cleave long dsRNA into short dsRNAs containing a 5'-$PO_4$ and a 2 nucleotide 3' overhang. Although the RNA cleaved by bacterial RNaseIII are generally smaller (12-15 bases in length) it leaves a 5'PO4 and a 2-nucleotide 3' overhang which is the same structure found on the RNA produced by DICER. A second approach would be to produce a mixture of siRNA and transfecting in the mixture of siRNA into the same reaction. The siRNA can be generated using a number of approaches currently methods for siRNA production-include chemical synthesis, in vitro synthesis using phase polymerase promoters, RNA dependant RNA polymerase or DNA vector based approaches.

Dicer is a eukaryotic protein that cleaves double-stranded RNA into 21-25 siRNA (Bernstein et al., 2001; Elbashir et al., 2001). The use of Dicer for in vitro generation of siRNA is problematic, however, because the reaction can be inefficient (Bernstein et al., 2001) and it is difficult to purify for in vitro application.

SUMMARY OF THE INVENTION

The present invention is based on the inventors' discovery that small interfering RNA's ("siRNA") can act as mediators of RNA interference ("RNAi").

In some embodiments, the invention concerns an siRNA that is capable of triggering RNA interference, a process by which a particular RNA sequence is destroyed. siRNA are dsRNA molecules that are 100 bases or fewer in length (or have 100 basepairs or fewer in its complementarity region). In some cases, it has a 2 nucleotide 3' overhang and a 5' phosphate. The particular RNA sequence is targeted as a result of the complementarity between the dsRNA and the particular RNA sequence. It will be understood that dsRNA or siRNA of the invention can effect at least a 20, 30, 40, 50, 60, 70, 80, 90 percent or more reduction of expression of a targeted RNA in a cell. dsRNA of the invention (the term "dsRNA" will be understood to include "siRNA") is distinct and distinguishable from antisense and ribozyme molecules by virtue of the ability to trigger RNAi. Structurally, dsRNA molecules for RNAi differ from antisense and ribozyme molecules in that dsRNA has at least one region of complementarity within the RNA molecule.

It is contemplated that a dsRNA may be a molecule comprising two separate RNA strands in which one strand has at least one region complementary to a region on the other strand. Alternatively, a dsRNA includes a molecule that is single stranded yet has at least one complementarity region as described above (see Sui et al., 2002 and Brummelkamp et al., 2002 in which a single strand with a hairpin loop is used as a dsRNA for RNAi). For convenience, lengths of dsRNA may be referred to in terms of bases, which simply refers to the length of a single strand or in terms of basepairs, which refers to the length of the complementarity region. It is specifically contemplated that embodiments discussed herein with respect to a dsRNA comprised of two strands are contemplated for use with respect to a dsRNA comprising a single strand, and vice versa. In a two-stranded dsRNA molecule, the strand that has a sequence that is complementary to the targeted mRNA is referred to as the "antisense strand" and the strand with a sequence identical to the targeted mRNA is referred to as the "sense strand." Similarly, with a dsRNA comprising only a single strand, it is contemplated that the "antisense region" has the sequence complementary to the targeted mRNA, while the "sense region" has the sequence identical to the targeted mRNA. Furthermore, it will be understood that sense and antisense region, like sense and antisense strands, are complementary (i.e., can specifically hybridize) to each other.

Strands or regions that are complementary may or may not be 100% complementary ("completely or fully complementary"). It is contemplated that sequences that are "complementary" include sequences that are at least 50% complementary, and may be at least 50%, 60%, 70%, 80%, or 90% complementary. In the range of 50% to 70% complementarity, such sequences may be referred to as "very complementary," while the range of greater than 70% to less than complete complementarity can be referred to as "highly complementary." Unless otherwise specified, sequences that are "complementary" include sequences that are "very complementary," "highly complementary," and "fully complementary." It is also contemplated that any embodiment discussed herein with respect to "complementary" strands or region can be employed with specifically "fully complementary," "highly complementary," and/or "very complementary" strands or regions, and vice versa. Thus, it is contemplated that in some instances that siRNA generated from sequence based on one organism may be used in a different organism to achieve RNAi of the cognate target gene. In other words, siRNA generated from a dsRNA that corresponds to a human gene may be used in a mouse cell if there is the requisite complementarity, as described above. Ultimately, the requisite threshold level of complementarity to achieve RNAi is dictated by functional capability.

It is specifically contemplated that there may be mismatches in the complementary strands or regions. Mismatches may number at most or at least 1, 2, 3, 4, 5, 6, 7, 8, 9, 10, 11, 12, 13, 14, 15, 16, 17, 18, 19, 20, 21, 22, 23, 24, 25 residues or more, depending on the length of the complentarity region.

In some embodiments, the strand or strands of dsRNA are 100 bases (or basepairs) or less, in which case they may also be referred to as "siRNA." In specific embodiments the strand or strands of the dsRNA are less than 70 bases in length. With respect to those embodiments, the dsRNA strand or strands may be from 5-70, 10-65, 20-60, 30-55, 40-50 bases or basepairs in length. In certain aspects, the strands are 5, 6, 7, 8, 9, 10, 11, 12, 13, 14, 15, 16, 17, 18, 19, or 20 base pairs in length. A dsRNA that has a complementarity region equal to or less than 30 basepairs (such as a single stranded hairpin RNA in which the stem or complementary portion is less than or equal to 30 basepairs) or one in which the strands are 30 bases or fewer in length is specifically contemplated, as such molecules begin to evade a mammalian's cell antiviral response. Thus, a hairpin dsRNA (one strand) may be 70 or fewer bases in length with a complementary region of 30 basepairs or fewer. In some cases, a dsRNA may be processed in the cell into siRNA.

Furthermore, it is contemplated that siRNA or the longer dsRNA template may be labeled. The label may be fluorescent, radioactive, enzymatic, or colorimetric. When two or more differentially colored labels are employed, fluorescent resonance energy transfer (FRET) techniques may be employed to characterize the dsRNA. Labels contemplated for use in several embodiments are non-radioactive. In many embodiments of the invention, the labels are fluorescent, though they may be enzymatic, radioactive, or positron emitters.

In some embodiments of the invention, a dsRNA has one or more non-natural nucleotides, such as a modified residue or a derivative or analog of a natural nucleotide. Any modified residue, derivative or analog may be used to the extent that it does not eliminate or substantially reduce (by at least 50%) RNAi activity of the dsRNA.

A person of ordinary skill in the art is well aware of achieving hybridization of complementary regions or molecules. Such methods typically involve heat and slow cooling of temperature during incubation.

Any cell that undergoes RNAi can be employed in methods of the invention. The cell may be a eukaryotic cell, mammalian cell such as a primate, rodent, rabbit, or human cell, a prokaryotic cell, or a plant cell. In some embodiments, the cell is alive, while in others the cell or cells is in an organism or tissue. Alternatively, the cell may be dead. The dead cell may also be fixed. In some cases, the cell is attached to a solid, non-reactive support such as a plate or petri dish. Such cells may be used for array analysis. It is contemplated that cells may be grown on an array and dsRNA administered to the cells.

In some methods of the invention, siRNA molecules or template nucleic acids may be isolated or purified prior to their being used in a subsequent step. SiRNA molecules may be isolated or purified prior to transfection into a cell. A template nucleic acid or amplification primer may be isolated or purified prior to it being transcribed or amplified. Isolation or purification can be performed by a number of methods known to those of skill in the art with respect to nucleic acids. In some embodiments, a gel, such as an agarose or acrylamide gel, is employed to isolate the siRNA.

Methods for generating siRNA to more than one target gene are considered part of the invention. Thus, siRNA or candidate siRNA directed to 1, 2, 3, 4, 5, 6, 7, 8, 9, 10 or more target genes may be generated and implemented in methods of the invention. An array can be created with pools of siRNA to multiple targets may be used as part of the invention.

In particular aspects of the present invention, there is disclosed an isolated RNA of from about 5 to about 20 nucleotides that mediates RNA interference of a target mRNA. In other non-limiting aspects, the isolated RNA can inactivate a corresponding gene by transcriptional silencing. In certain embodiments, the isolated RNA can be 5, 6, 7, 8, 9, 20, 11, 12, 13, 14, 15, 16, 17, 18, 19, 20, 21, 22, 23, 24, 25, or more nucleotides in length. The isolated RNA can further comprise a terminal 3' hydroxyl group or a 5' phosphate group, or both. The isolated RNA can be an siRNA. The siRNA can be a single or double stranded RNA. In particular aspects, the 3' or 5' or both ends of the double stranded RNA comprises a 1, 2, 3, 4, 5, 6, 7, 8, 9, 10, 11, 12, 13, 14, 15, 16, 17 or more nucleotide overhang. In certain embodiments, the nucleotide overhang is a 2 nucleotide overhang. The nucleotide overhang can include any combination of a thymine, uracil, adenine, guanine, or cytosine, or derivatives or analogues thereof. The nucleotide overhang in certain aspects is a 2 nucleotide overhang, where both nucleotides are thymine.

The isolated RNA can be made by any of the methods discussed throughout the specification. In particular embodiments the isolated RNA is chemically synthesized or is an analog of a naturally occurring RNA. In other embodiments, the isolated RNA is formulated into a pharmaceutically acceptable composition.

The isolated RNA can also associate with a protein complex. In certain aspects, the isolated RNA is associated with or bound to a protein complex. In non-limiting embodiments, the protein complex is RNA-induced silencing complex (RISC).

In more particular aspects, the isolated RNA comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13; SEQ ID NO: 14, SEQ ID NO: 15, SEQ ID NO: 16, SEQ ID NO: 17; SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30; SEQ ID NO: 31, SEQ ID NO: 32, SEQ ID NO: 33, SEQ ID NO: 34, SEQ ID NO 35, SEQ ID NO: 36; SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, and SEQ ID NO: 54.

The inventors also contemplate analogs of the isolated RNAs described throughout the specification. The analog can differ from the isolated RNA by the addition, deletion, substitution or alteration of one or more nucleotides. Non-limiting examples of the different types of nucleotides that can be use with the present invention are described throughout the specification.

In yet another embodiment of the present invention there is provided a method of reducing expression of a target gene in a cell comprising obtaining at least one siRNA of 5-100 or more nucleotides in length and delivering the siRNA into the cell. The siRNA can be from about 10 to about 90, 20, to about 80, 30 to about 70, 40 to about 60, to about 50 nucleotides in length. In specific aspects, the siRNA is from about 3, 4, 5, 6, 7, 8, 9, 10, 11, 12, 13, 14, 15, 16, 17, 18, 19 to about 20 nucleotides in length. Delivery of the siRNA into a cell can be performed by any numerous ways that are known to a person of ordinary skill in the art and that are described throughout this specification. There are certain embodiments where at least two siRNAs are obtained and are subsequently delivered into the cell. Other aspects include obtaining a pool of siRNAs and delivering the pool into the cell. As noted above and throughout the specification, the siRNAs of the present invention can be made by many methods. In particular aspects, the siRNAs are chemically synthesized or are an analog of a naturally occurring siRNA. There are certain instances of the invention where the siRNA is isolated prior to its delivery into the cell. Isolating and purifying siRNAs are known in the art and are described throughout the specification. Isolating the siRNA can be done prior to or after delivery into the cell. In non-limiting embodiments, the cell can be comprised in an organism. The organism, in non-limiting examples, can be a human, dog, rat, mouse, pig, rabbit, or cow. The cell can be a human or non-human cell. In certain aspects, at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more siRNA molecules are delivered into the cell. The siRNAs can be the same or different siRNAs with different target mRNAs.

In still another aspect of the present invention, there is provided a method of mediating RNA interference of mRNA of a gene in a cell or organism comprising (a) introducing RNA of from about 5 to about 20 nucleotides which targets the mRNA of the gene for degradation into the cell or organism and maintaining the cell or organism produced in (a) under conditions under which degradation of the mRNA occurs, thereby mediating RNA interference of the mRNA of the gene in the cell or organism. The RNA can be a chemically synthesized RNA or an analog of naturally occurring RNA. The RNA can be an siRNA that is from about 3, 4, 5, 6, 7, 8, 9, 10, 11, 12, 13, 14, 15, 16, 17, 18, 19, or 20, or more nucleotides in length. The gene can be any number of genes that are described throughout the specification and that are known to a person of ordinary skill in the art. In certain embodiments, the gene encodes a cellular mRNA or a viral mRNA.

Another embodiment includes a method of mediating RNA interference of mRNA of a gene in a cell or organism in which RNA interference occurs, comprising introducing into the cell or organism RNA of from about 5 to about 20 nucleotides that mediates RNA interference of mRNA of the gene, thereby producing a cell or organism that contains the RNA; and maintaining the cell or organism that contains the RNA under conditions under which RNA interference occurs, thereby mediating RNA interference of mRNA of the gene in the cell or organism. As discussed throughout, in non-limiting examples, the RNA can be an siRNA that is from about 3, 4, 5, 6, 7, 8, 9, 10, 11, 12, 13, 14, 15, 16, 17, 18, 19, or 20, or more nucleotides in length. The siRNA can be chemically synthesized or an analog of RNA that mediates RNA interference.

In certain aspects, the inventors contemplate a knockdown cell or organism generated by any one of the methods disclosed throughout this specification. The knockdown cell or organism can mimic a disease state.

There is also disclosed a method of examining the function of a gene in a cell or organism comprising (a) introducing RNA of from about 5 to about 20 nucleotides that targets mRNA of the gene for degradation into the cell or organism, thereby producing a test cell or test organism; (b) maintaining the test cell or test organism under conditions under which degradation of mRNA of the gene occurs, thereby producing a test cell or test organism in which mRNA of the gene is degraded; and (c) observing the phenotype of the test cell or test organism produced in (b). In non-limiting examples, the RNA can be an siRNA that is from about 3, 4, 5, 6, 7, 8, 9, 10, 11, 12, 13, 14, 15, 16, 17, 18, 19, or 20, or more nucleotides in length. The siRNA can be chemically synthesized or an analog of RNA that mediates RNA interference. The method can further comprise comparing the phenotype observed to that of an appropriate control cell or control organism, thereby providing information about the function of the gene.

Other aspects of the present invention include a composition comprising biochemical components of a cell that target mRNA of a gene to be degraded by RNA of about 5 to about 20 nucleotides in length. In non-limiting examples, the RNA can be an siRNA that is from about 3, 4, 5, 6, 7, 8, 9, 10, 11, 12, 13, 14, 15, 16, 17, 18, 19, or 20, or more nucleotides in length. The siRNA can be chemically synthesized or an analog of RNA that mediates RNA interference.

In still another embodiment of the present invention, there is provided a method of treating a disease or condition associated with the presence of a protein in an individual comprising administering to the individual RNA of from about 5 to about 20 nucleotides that targets the mRNA of the protein for degradation. In non-limiting examples, the RNA can be an siRNA that is from about 3, 4, 5, 6, 7, 8, 9, 10, 11, 12, 13, 14, 15, 16, 17, 18, 19, or 20, or more nucleotides in length. The siRNA can be chemically synthesized or an analog of RNA that mediates RNA interference.

Another method contemplated by the present invention includes a method of assessing whether an agent acts on a gene product comprising: (a) introducing RNA of from about 5 to about 20 nucleotides which targets the mRNA of the gene for degradation into a cell or organism; (b) maintaining the cell or organism of (a) under conditions in which degradation of the mRNA occurs; (c) introducing the agent into the cell or organism of (b); and (d) determining whether the agent has an effect on the cell or organism, wherein if the agent has no effect on the cell or organism then the agent acts on the gene product or on a biological pathway that involves the gene product. In non-limiting examples, the RNA can be an siRNA that is from about 3, 4, 5, 6, 7, 8, 9, 10, 11, 12, 13, 14, 15, 16, 17, 18, 19, or 20, or more nucleotides in length. The siRNA can be chemically synthesized or an analog of RNA that mediates RNA interference.

There is also provided a method of assessing whether a gene product is a suitable target for drug discovery comprising: (a) introducing RNA of from about 5 to about 20 nucleotides which targets the mRNA of the gene for degradation into a cell or organism; (b) maintaining the cell or organism of (a) under conditions in which degradation of the mRNA occurs resulting in decreased expression of the gene; and (c) determining the effect of the decreased expression of the gene on the cell or organism, wherein if decreased expression has an effect, then the gene product is a target for drug discovery. In non-limiting examples, the RNA can be an siRNA that is from about 3, 4, 5, 6, 7, 8, 9, 10, 11, 12, 13, 14, 15, 16, 17, 18, 19, or 20, or more nucleotides in length. The siRNA can be chemically synthesized or an analog of RNA that mediates RNA interference.

Also contemplated is a gene identified by the sequencing of endogenous 5 to 20 nucleotide RNA molecules that mediate RNA interference. In non-limiting examples, the RNA can be an siRNA that is from about 3, 4, 5, 6, 7, 8, 9, 10, 11, 12, 13, 14, 15, 16, 17, 18, 19, or 20, or more nucleotides in length. The siRNA can be chemically synthesized or an analog of RNA that mediates RNA interference.

As discussed above and throughout the specification, there is also provided a pharmaceutical composition comprising RNA of from about 5 to about 20 nucleotides that mediates RNA interference and an appropriate carrier. In non-limiting examples, the RNA can be an siRNA that is from about 3, 4, 5, 6, 7, 8, 9, 10, 11, 12, 13, 14, 15, 16, 17, 18, 19, or 20, or more nucleotides in length. The siRNA can be chemically synthesized or an analog of RNA that mediates RNA interference.

In still another aspect, there is disclosed a method of producing knockdown cells, comprising introducing into cells in which a gene is to be knocked down RNA of about 5 to about 20 nucleotides that targets the mRNA corresponding to the gene and maintaining the resulting cells under conditions under which RNA interference occurs, resulting in degradation of the mRNA of the gene, thereby producing knockdown cells. In non-limiting examples, the RNA can be an siRNA that is from about 3, 4, 5, 6, 7, 8, 9, 10, 11, 12, 13, 14, 15, 16, 17, 18, 19, or 20, or more nucleotides in length. The siRNA can be chemically synthesized or an analog of RNA that mediates RNA interference.

An additional embodiment of the present invention includes an isolated DNA comprising DNA encoding RNA that is processed in eukaryotic cells to RNA segments of about 5 to about 20 nucleotides in length that inactivate a corresponding gene by transcriptional silencing or that mediate RNA interference of mRNA of a gene, or that target mRNA of a protein for degradation. In non-limiting examples, the RNA can be an siRNA that is from about 3, 4, 5, 6, 7, 8, 9, 10, 11, 12, 13, 14, 15, 16, 17, 18, 19, or 20, or more nucleotides in length.

In certain embodiments, there is provided a kit that includes an RNA of from about 5 to about 20 nucleotides that mediates RNA interference of a target mRNA, that inactivate a corresponding gene by transcriptional silencing, or that targets mRNA of a protein for degradation. In non-limiting examples, the RNA can be an siRNA that is from about 3, 4, 5, 6, 7, 8, 9, 10, 11, 12, 13, 14, 15, 16, 17, 18, 19, or 20, or more nucleotides in length. The siRNA can be chemically synthesized or an analog of RNA that mediates RNA interference. Other aspects of the kits of the present invention are described throughout the specification.

It is specifically contemplated that any method of the invention may be employed with any kit component or composition described herein. Furthermore, any kit may contain any component described herein and any component involved in any method of the invention. Thus, any element discussed with respect to one embodiment may be applied to any other embodiment of the invention.

It is contemplated that the use of the term "about" in the context of the present invention is to connote inherent problems with precise measurement of a specific element, characteristic, or other trait. Thus, the term "about," as used herein in the context of the claimed invention, simply refers to an amount or measurement that takes into account single or collective calibration and other standardized errors generally associated with determining that amount or measurement. For example, a concentration of "about" 100 mM of Tris can encompass an amount of 100 mM±5 mM, if 5 mM represents the collective error bars in arriving at that concentration. Thus, any measurement or amount referred to in this application can be used with the term "about" if that measurement or amount is susceptible to errors associated with calibration or measuring equipment, such as a scale, pipetteman, pipette, graduated cylinder, etc.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method, kit, reagent, or composition of the invention, and vice versa. Furthermore, compositions of the invention can be used to achieve methods of the invention.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
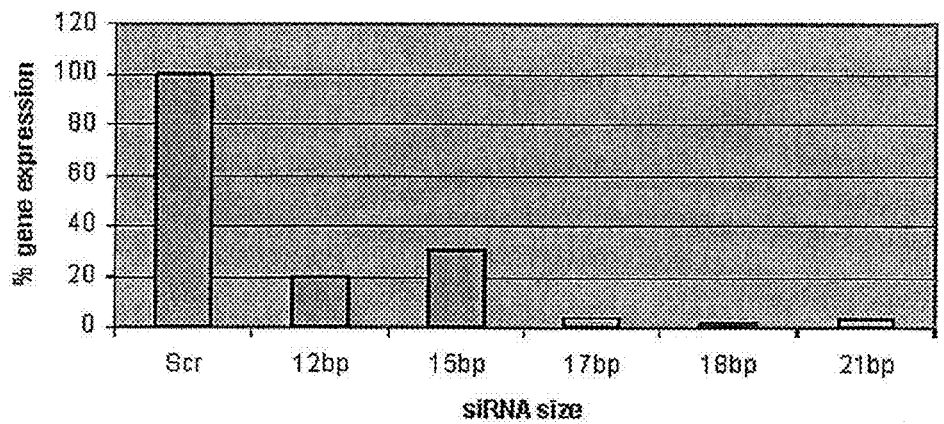
FIG. 1A-FIG. 1B. Analysis of chemically synthesized siRNA of varying lengths targeting GFP. Smaller siRNAs were able to knock down the expression of GFP.

The present invention concerns nucleic acid molecules that can be used in the process of RNA interference (RNAi). RNAi results in a reduction of expression of a particular target. Double stranded RNA has been shown to reduce gene expression of a target. A portion of one strand of the double stranded RNA is complementary to a region of the target's mRNA while another portion of the double stranded RNA molecule is identical to the same region of the target's mRNA. Discussed below are uses for the present invention—compositions, methods, and kits—and ways of implementing the invention.

I. RNA Interference (RNAi)

RNA interference (also referred to as "RNA-mediated interference") (RNAi) is a mechanism by which gene expression can be reduced or eliminated. Double stranded RNA (dsRNA) has been observed to mediate the reduction, which is a multi-step process. dsRNA activates post-transcriptional gene expression surveillance mechanisms that appear to function to defend cells from virus infection and transposon activity. (Fire et al., 1998; Grishok et al., 2000; Ketting et al., 1999; Lin et al., 1999; Montgomery et al., 1998; Sharp et al., 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene. (Fire et al., 1998; Grishok et al., 2000; Ketting et al., 1999; Lin et al., 1999; Montgomery et al., 1998; Sharp, 1999; Sharp et al., 2000; Tabara et al., 1999). Moreover, dsRNA has been shown to silence genes in a wide range of systems, including plants, protozoans, fungi, *C. elegans, Trypanasoma, Drosophila*, and mammals (Grishok et al., 2000; Sharp, 1999; Sharp et al., 2000; Elbashir et al., 2001).

RNAi can be passed to progeny, both through injection into the gonad or by introduction into other parts of the body (including ingestion) followed by migration to the gonad. Several principles are worth noting (see Plasterk and Ketting, 2000). First, the dsRNA is typically directed to an exon, although some exceptions to this have been shown. Second, a homology threshold (probably about 80-85% over 200 bases) is required. Most tested sequences are 500 base pairs or greater, though sequences of 30 nucleotides or fewer evade the antiviral response in mammalian cells. (Baglioni et al., 1983; Williams, 1997). Third, the targeted mRNA is lost after RNAi. Fourth, the effect is non-stoichiometric, and thus incredibly potent. In fact, it has been estimated that only a few copies of dsRNA are required to knock down >95% of targeted gene expression in a cell (Fire et al., 1998).

Although the precise mechanism of RNAi is still unknown, the involvement of permanent gene modification or the disruption of transcription have been experimentally eliminated. It is now generally accepted that RNAi acts post-transcriptionally, targeting RNA transcripts for degradation. It appears that both nuclear and cytoplasmic RNA can be targeted. (Bosher et al., 2000).

Some of the uses for RNAi include identifying genes that are essential for a particular biological pathway, identifying disease-causing genes, studying structure function relationships, and implementing therapeutics and diagnostics. As with other types of gene inhibitory compounds, such as antisense and triplex forming oligonucleotides, tracking these potential drugs in vivo and in vitro is important for drug development, pharmacokinetics, biodistribution, macro and microimaging metabolism and for gaining a basic understanding of how these compounds behave and function. siRNAs have high specificity and may perhaps be used to knock out the expression of a single allele of a dominantly mutated diseased gene.

A. Nucleic Acids for RNAi

The present invention concerns double-stranded RNA capable of triggering RNAi. The RNA may be synthesized chemically or it may be produced recombinantly. They may be subsequently isolated and/or purified.

As used herein, the term "dsRNA" refers to a double-stranded RNA molecule. The molecule may be a single strand with intra-strand complementarity such that two portions of the strand hybridize with each other or the molecule may be two separate RNA strands that are partially or fully complementary to each other along one or more regions or along their entire lengths. Partially complementary means the regions are less than 100% complementary to each other, but that they are at least 50%, 60%, 70%, 80%, or 90% complementary to each other.

The siRNA provided by the present invention allows for the modulation and especially the attenuation of target gene expression when such a gene is present and liable to expression within a cell. Modulation of expression can be partial or complete inhibition of gene function, or even the up-regulation of other, secondary target genes or the enhancement of expression of such genes in response to the inhibition of the primary target gene. Attenuation of gene expression may include the partial or complete suppression or inhibition of gene function, transcript processing or translation of the transcript. In the context of RNA interference, modulation of gene expression is thought to proceed through a complex of proteins and RNA, specifically including small, dsRNA that may act as a "guide" RNA. The siRNA therefore is thought to be effective when its nucleotide sequence sufficiently corresponds to at least part of the nucleotide sequence of the target gene. Although the present invention is not limited by this mechanistic hypothesis, it is preferred that the sequence of nucleotides in the siRNA be substantially identical to at least a portion of the target gene sequence.

A target gene generally means a polynucleotide comprising a region that encodes a polypeptide, or a polynucleotide region that regulates replication, transcription or translation or other processes important to expression of the polypeptide, or a polynucleotide comprising both a region that encodes a polypeptide and a region operably linked thereto that regulates expression. The targeted gene can be chromosomal (genomic) or extrachromosomal. It may be endogenous to the cell, or it may be a foreign gene (a transgene). The foreign gene can be integrated into the host genome, or it may be present on an extrachromosomal genetic construct such as a plasmid or a cosmid. The targeted gene can also be derived from a pathogen, such as a virus, bacterium, fungus or protozoan, which is capable of infecting an organism or cell. Target genes may be viral and pro-viral genes that do not elicit the interferon response, such as retroviral genes. The target gene may be a protein-coding gene or a non-protein coding gene, such as a gene which codes for ribosomal RNAs, splicosomal RNA, tRNAs, etc.

Any gene being expressed in a cell can be targeted. Preferably, a target gene is one involved in or associated with the progression of cellular activities important to disease or of particular interest as a research object. Thus, by way of example, the following are classes of possible target genes that may be used in the methods of the present invention to modulate or attenuate target gene expression: developmental genes (e.g. adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), oncogenes (e.g. ABLI, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES), tumor suppresser genes (e.g. APC, BRCA1, BRCA2, MADH4, MCC, NF1, NF2, RB1, TP53 and WT1), and enzymes (e.g. ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, galactosidases, glucanases, glucose oxidases, GTPases, helicases, hemicellulases, integrases, invertases, isomersases, kinases, lactases, lipases, lipoxygenases, lysozymes, pectinesterases, peroxidases, phosphatases, phospholipases, phosphorylases, polygalacturonases, proteinases and peptideases, pullanases, recombinases, reverse transcriptases, topoisomerases, xylanases).

The nucleotide sequence of the siRNA is defined by the nucleotide sequence of its target gene. The siRNA contains a nucleotide sequence that is essentially identical to at least a portion of the target gene. Preferably, the siRNA contains a nucleotide sequence that is completely identical to at least a portion of the target gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

A siRNA comprises a double stranded structure, the sequence of which is "substantially identical" to at least a portion of the target gene. "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated. See, for example: Computational Molecular Biology, Lesk, A. M., ed. Oxford University Press, New York, 1988; Biocomputing: Informatics and Genome Projects, Smith, D. W., ed., Academic Press, New York, 1993; and the methods disclosed in WO 99/32619, WO 01/68836, WO 00/44914, and WO 01/36646, specifically incorporated herein by reference. While a number of methods exist for measuring identity between two nucleotide sequences, the term is well known in the art. Methods for determining identity are typically designed to produce the greatest degree of matching of nucleotide sequence and are also typically embodied in computer programs. Such programs are readily available to those in the relevant art. For example, the GCG program package (Devereux et al.), BLASTP, BLASTN, and FASTA (Atschul et al.) and CLUSTAL (Higgins et al., 1992; Thompson, et al., 1994).

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. It is preferred that there be 100% sequence identity between the dsRNA for use as siRNA and at least 15 contiguous nucleotides of the target gene, although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

RNA (ribonucleic acid) is known to be the transcription product of a molecule of DNA (deoxyribonucleic acid) synthesized under the action of an enzyme, DNA-dependent RNA polymerase. There are diverse applications of the obtaining of specific RNA sequences, such as, for example, the synthesis of RNA probes or of oligoribonucleotides (Milligan et al.), or the expression of genes (see, in particular, Steen et al., Fuerst, et al. and Patent Applications WO 91/05, 866 and EP 0,178,863), or alternatively gene amplification as described by Kievits, et al. and Kwoh et al. or in Patent Applications WO 88/10,315 and WO 91/02,818, and U.S. Pat. No. 5,795,715, all of which are expressly incorporated herein by reference.

One of the distinctive features of most DNA-dependent RNA polymerases is that of initiating RNA synthesis according to a DNA template from a particular start site as a result of the recognition of a nucleic acid sequence, termed a promoter, which makes it possible to define the precise localization and the strand on which initiation is to be effected. Contrary to DNA-dependent DNA polymerases, polymerization by DNA-dependent RNA polymerases is not initiated from a 3'-OH end, and their natural substrate is an intact DNA double strand.

Compared to bacterial, eukaryotic or mitochondrial RNA polymerases, phage RNA polymerases are very simple enzymes. Among these, the best known are the RNA polymerases of bacteriophages T7, T3 and SP6. These enzymes are very similar to one another, and are composed of a single subunit of 98 to 100 kDa. Two other phage polymerases share these similarities: that of *Klebsiella* phage K11 and that of phage BA14 (Diaz et al.). Any DNA dependent RNA polymerase is expected to perform in conjunction with a functionally active promoter as desired in the present invention. These include, but are not limited to the above listed polymerases, active mutants thereof, *E. coli* RNA polymerase, and RNA polymerases I, II, and III from a variety of eukaryotic organisms.

Initiation of transcription with T7, SP6 RNA and T3 RNA Polymerases is highly specific for the T7, SP6 and T3 phage promoters, respectively. The properties and utility of these polymerases are well known to the art. Their properties and sources are described in U.S. Pat. Nos. (T7) 5,869,320; 4,952, 496; 5,591,601; 6,114,152; (SP6) 5,026,645; (T3) 5,102,802; 5,891,681; 5,824,528; 5,037,745, all of which are expressly incorporated herein by reference.

Reaction conditions for use of these RNA polymerases are well known in the art, and are exemplified by those conditions provided in the examples and references. The result of contacting the appropriate template with an appropriate polymerase is the synthesis of an RNA product, which is typically single-stranded. Although under appropriate conditions, double stranded RNA may be made from a double stranded DNA template. See U.S. Pat. No. 5,795,715, incorporated herein by reference. The process of sequence specific synthesis may also be known as transcription, and the product the transcript, whether the product represents an entire, functional gene product or not.

dsRNA for use as siRNA may also be enzymatically synthesized through the use of RNA dependent RNA polymerases such as Q beta replicase, Tobacco mosaic virus replicase, brome mosaic virus replicase, potato virus replicase, etc. Reaction conditions for use of these RNA polymerases are well known in the art, and are exemplified by those conditions provided in the examples and references. Also see U.S. Pat. No. RE35,443, and U.S. Pat. No. 4,786,600, both of which are incorporated herein by reference. The result of contacting the appropriate template with an appropriate polymerase is the synthesis of an RNA product, which is typically double-stranded. Employing these RNA dependent RNA polymerases therefore may utilize a single stranded RNA or single stranded DNA template. If utilizing a single stranded DNA template, the enzymatic synthesis results in a hybrid RNA/DNA duplex that is also contemplated as useful as siRNA.

The templates for enzymatic synthesis of siRNA are nucleic acids, typically, though not exclusively DNA. A nucleic acid may be made by any technique known to one of ordinary skill in the art. Non-limiting examples of synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. No. 5,705,629, each incorporated herein by reference, or as described in WO 2003/106630 which is incorporated herein by reference.

A non-limiting example of enzymatically produced nucleic acid include one produced by enzymes in amplification reactions such as PCR™ (see for example, U.S. Pat. Nos. 4,683,202 and 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells (see for example, Sambrook, 2001, incorporated herein by reference).

The term "nucleic acid" will generally refer to at least one molecule or strand of DNA, RNA or a derivative or mimic thereof, comprising at least one nucleotide base, such as, for example, a naturally occurring purine or pyrimidine base found in DNA (e.g., adenine "A," guanine "G," thymine "T," and cytosine "C") or RNA (e.g. A, G, uracil "U," and C). The term "nucleic acid" encompasses the terms "oligonucleotide" and "polynucleotide." These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule.

As will be appreciated by one of skill in the art, the useful form of nucleotide or modified nucleotide to be incorporated will be dictated largely by the nature of the synthesis to be performed. Thus, for example, enzymatic synthesis typically utilizes the free form of nucleotides and nucleotide analogs, typically represented as nucleotide triphospates, or NTPs. These forms thus include, but are not limited to aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NH$_2$ UTP, 2'NH$_2$ CTP, and 2' F UTP. As will also be appreciated by one of skill in the art, the useful form of nucleotide for chemical syntheses may be typically represented as aminoallyl uridine, pseudo-uridine, 5-I-uridine, 5-I-cytidine, 5-Br-uridine, alpha-S adenosine, alpha-S cytidine, alpha-S guanosine, alpha-S uridine, 4-thio uridine, 2-thio-cytidine, 2'NH$_2$ uridine, 2'NH$_2$ cytidine, and 2' F uridine. In the present invention, the listing of either form is non-limiting in that the choice of nucleotide form will be dictated by the nature of the synthesis to be performed. In the present invention, then, the inventors use the terms aminoallyl uridine, pseudo-uridine, 5-I-uridine, 5-I-cytidine, 5-Br-uridine, alpha-S adenosine, alpha-S cytidine, alpha-S guanosine, alpha-S uridine, 4-thio uridine, 2-thio-cytidine, 2'NH$_2$ uridine, 2'NH$_2$ cytidine, and 2' F uridine generically to refer to the appropriate nucleotide or modified nucleotide, including the free phosphate (NTP) forms as well as all other useful forms of the nucleotides.

In certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In other particular aspects, the gene comprises a nucleic acid, and/or encodes a polypeptide or peptide-coding sequences of a gene that is defective or mutated in a hematopoietic and lympho-hematopoietic disorder. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit. As will be understood by those in the art, this functional term "gene" includes both genomic sequences, RNA or cDNA sequences, or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like. Thus, a "truncated gene" refers to a nucleic acid sequence that is missing a stretch of contiguous nucleic acid residues.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended protocol.

To obtain the RNA corresponding to a given template sequence through the action of an RNA polymerase, it may require placing the target sequence under the control of the promoter recognized by the RNA polymerase.

The spacing between promoter elements frequently is flexible, so that promoter function is preserved when elements are inverted or moved relative to one another. The spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

T7, T3, or SP6 RNA polymerases display a high fidelity to their respective promoters. The natural promoters specific for the RNA polymerases of phages T7, T3 and SP6 are well known. Furthermore, consensus sequences of promoters are known to be functional as promoters for these polymerases. The bacteriophage promoters for T7, T3, and SP6 consist of 23 by numbered −17 to +6, where +1 indicates the first base of the coded transcript. An important observation is that, of the +1 through +6 bases, only the base composition of +1 and +2 are critical and must be a G and purine, respectively, to yield an efficient transcription template. In addition, synthetic oligonucleotide templates only need to be double-stranded in the −17 to −1 region of the promoter, and the coding region can be all single-stranded. (See Milligan et al.) This can reduce the cost of synthetic templates, since the coding region (i.e., from +1 on) can be left single-stranded and the short oligonucleotides required to render the promoter region double-stranded can be used with multiple templates. A further discussion of consensus promoters and a source of naturally occurring bacteriophage promoters is U.S. Pat. No. 5,891,681, specifically incorporated herein by reference.

Use of a T7, T3 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

When made in vitro, siRNA is formed from one or more strands of polymerized ribonucleotide. When formed of only one strand, it takes the form of a self-complementary hairpin-type or stem and loop structure that doubles back on itself to form a partial duplex. The self-duplexed portion of the RNA molecule may be referred to as the "stem" and the remaining, connecting single stranded portion referred to as the "loop" of the stem and loop structure. When made of two strands, they are substantially complementary.

It is contemplated that the region of complementarity in either case is at least 5 contiguous residues, though it is specifically contemplated that the region is at least or at most 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides. It is further understood that the length of complementarity between the dsRNA and the targeted mRNA may be any of the lengths identified above. Included within the term "dsRNA" is small interfering RNA (siRNA), which are generally 12-15 or 21-23 nucleotides in length and which possess the ability to mediate RNA interference. It is contemplated that siRNAs of the present invention may be 5, 6, 7, 8, 9, 10, 11, 12, 13, 14, 15, 16, 17, 18, 19, 20, 21, 22, 23, 24, 25, 26, 27, 28, 29, 30 or more basepairs in length.

dsRNA capable of triggering RNAi has one region that is complementary to the targeted mRNA sequence and another region that is identical to the targeted mRNA sequence. Of course, it is understood that an mRNA is derived from genomic sequences or a gene. In this respect, the term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants.

A dsRNA may be of the following lengths, or be at least or at most of the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs. It will be understood that these lengths refer either to a single strand of a two-stranded dsRNA molecule or to a single stranded dsRNA molecule having portions that form a double-stranded molecule.

Furthermore, outside regions of complementarity, there may be a non-complementarity region that is not complementary to another region in the other strand or elsewhere on a single strand. Non-complementarity regions may be at the 3', 5' or both ends of a complementarity region and they may number 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 5, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more bases.

The term "recombinant" may be used and this generally refers to a molecule that has been manipulated in vitro or that is the replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. The use of "dsRNA" encompasses both "oligonucleotides" and "polynucleotides," unless otherwise specified.

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

1. Nucleic Acid Molecules
    a. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moeities comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. In the table below, non-limiting, purine and pyrimidine derivatives and analogs are also provided.

TABLE 3

Purine and Pyrmidine Derivatives or Analogs

| Abbr. | Modified base description |
|---|---|
| ac4c | 4-acetylcytidine |
| Chm5u | 5-(carboxyhydroxylmethyl) uridine |
| Cm | 2'-O-methylcytidine |
| Cmnm5s2u | 5-carboxymethylamino-methyl-2-thioridine |
| Cmnm5u | 5-carboxymethylaminomethyluridine |
| D | Dihydrouridine |
| Fm | 2'-O-methylpseudouridine |
| Gal q | Beta,D-galactosylqueosine |
| Gm | 2'-O-methylguanosine |
| I | Inosine |
| I6a | N6-isopentenyladenosine |
| m1a | 1-methyladenosine |
| m1f | 1-methylpseudouridine |
| m1g | 1-methylguanosine |
| m1I | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| Mam5u | 5-methylaminomethyluridine |

TABLE 3-continued

Purine and Pyrimidine Derivatives or Analogs

| Abbr. | Modified base description |
|---|---|
| Mam5s2u | 5-methoxyaminomethyl-2-thiouridine |
| Man q | Beta,D-mannosylqueosine |
| Mcm5s2u | 5-methoxycarbonylmethyl-2-thiouridine |
| Mcm5u | 5-methoxycarbonylmethyluridine |
| Mo5u | 5-methoxyuridine |
| Ms2i6a | 2-methylthio-N6-isopentenyladenosine |
| Ms2t6a | N-((9-beta-D-ribofuranosyl-2-methylthiopurine-6-yl)carbamoyl)threonine |
| Mt6a | N-((9-beta-D-ribofuranosylpurine-6-yl)N-methyl-carbamoyl)threonine |
| Mv | Uridine-5-oxyacetic acid methylester |
| o5u | Uridine-5-oxyacetic acid (v) |
| Osyw | Wybutoxosine |
| P | Pseudouridine |
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-((9-beta-D-ribofuranosylpurine-6-yl)carbamoyl)threonine |
| Tm | 2'-O-methyl-5-methyluridine |
| Um | 2'-O-methyluridine |
| Yw | Wybutosine |
| X | 3-(3-amino-3-carboxypropyl)uridine, (acp3)u |

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

b. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

c. Nucleotides

As used herein, a "nucleotide" refers to a nucleoside further comprising a "backbone moiety." A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. Other types of attachments are known in the art, particularly when a nucleotide comprises derivatives or analogs of a naturally occurring 5-carbon sugar or phosphorus moiety.

d. Nucleic Acid Analogs

A nucleic acid may comprise, or be composed entirely of, a derivative or analog of a nucleobase, a nucleobase linker moiety and/or backbone moiety that may be present in a naturally occurring nucleic acid. dsRNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652, 099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified 2'-deoxyfuranosyl moieties) used in nucleic acid detection; U.S. Pat. No. 5,446, 137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466, 786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777, 092, 5,623,070, 5,610,289 and 5,602,240, which describe oligonucleotides with three or four atom linker moiety replacing phosphodiester backbone moiety used for improved nuclease resistance, cellular uptake and regulating RNA expression; U.S. Pat. No. 5,858,988, which describes hydrophobic carrier agent attached to the 2'-O position of oligonucleotides to enhanced their membrane permeability and stability; U.S. Pat. No. 5,214,136, which describes oligonucleotides conjugaged to anthraquinone at the 5' terminus that possess enhanced hybridization to DNA or RNA;

enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and U.S. Pat. No. 5,480,980 (7-deaza-2' deoxyguanosine nucleotides and nucleic acid analogs thereof).

2. Preparation of Nucleic Acids

The present invention concerns various nucleic acids in different embodiments of the invention. In some embodiments, dsRNA is created by transcribing a DNA template. The DNA template may be comprised in a vector or it may be a non-vector template. Alternatively, a dsRNA may be created by hybridizing two synthetic, complementary RNA molecules or hybridizing a single synthetic RNA molecule with at least one complementarity region. Such nucleic acids may be made by any technique known to one of ordinary skill in the art, such as for example, chemical synthesis, enzymatic production or biological production.

a. Vectors

Nucleic acids of the invention, particularly DNA templates, may be produced recombinantly. Protein and polypeptides may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., (2001) and Ausubel et al., 1994, both incorporated by reference. A vector may encode non-template sequences such as a tag or label. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter (examples include the bacterial promoters SP6, T3, and T7), which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it may be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (2001), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Other elements of a vector are well known to those of skill in the art. A vector may include a polyadenylation signal, an initiation signal, an internal ribosomal binding site, a multiple cloning site, a selective or screening marker, a termination signal, a splice site, an origin of replication, or a combination thereof.

b. In Vitro Synthesis of dsRNA

A DNA template may be used to generate complementing RNA molecule(s) to generate a double-stranded RNA molecule. One or two DNA templates may be employed to generate a dsRNA. In some embodiments, the DNA template can be part of a vector or plasmid, as described herein. Alternatively, the DNA template for RNA may be created by an amplification method.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred. Pairs of primers designed to selectively hybridize to nucleic acids corresponding to the target gene are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification are conducted until a sufficient amount of product is produced.

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety. A reverse transcriptase PCR™ amplification procedure may be performed to quantify the amount of mRNA amplified. Methods of reverse transcribing RNA into cDNA are well known (see Sambrook et al., 2001). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assy (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety. Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase copies the replicative sequence which may then be detected. An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). EP Application 329 822 disclose a nucleic acid amplification process involving cyclically synthesizing ssRNA, ssDNA, and dsDNA, which may be used in accordance with the present invention. PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

c. Chemical Synthesis

Nucleic acid synthesis is performed according to standard methods. See, for example, Itakura and Riggs (1980). Additionally, U.S. Pat. Nos. 4,704,362, 5,221,619, and 5,583,013 each describe various methods of preparing synthetic nucleic acids. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

Diester method. The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester method. The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide phosphorylase method. This is an enzymatic method of DNA synthesis that can be used to synthesize many useful oligonucleotides (Gillam et al., 1978; Gillam et al., 1979). Under controlled conditions, polynucleotide phosphorylase adds predominantly a single nucleotide to a short oligonucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-phase methods. Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

3. Nucleic Acid Purification

A nucleic acid may be purified on polyacrylamide gels, cesium chloride centrifugation gradients, or by any other means known to one of ordinary skill in the art (see for example, Sambrook (2001), incorporated herein by reference). Alternatively, a column, filter, or cartridge containing an agent that binds to the nucleic acid, such as a glass fiber, may be employed.

Following any amplification or transcription reaction, it may be desirable to separate the amplification or transcription product from the template and/or the excess primer. In one embodiment, products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Nucleic Acid Transfer

Suitable methods for nucleic acid delivery to effect RNAi according to the present invention are believed to include virtually any method by which a nucleic acid (e.g., DNA, RNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981, 274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

There are a number of ways in which expression vectors may be introduced into cells to generate dsRNA. In certain embodiments of the invention, the expression vector comprises a virus or engineered vector derived from a viral genome, while in other embodiments, it is a nonviral vector. Other expression systems are also readily available.

5. Host Cells and Target Cells

The cell containing the target gene may be derived from or contained in any organism (e.g., plant, animal, protozoan, virus, bacterium, or fungus). The plant may be a monocot, dicot or gynmosperm; the animal may be a vertebrate or invertebrate. Preferred microbes are those used in agriculture or by industry, and those that a pathogenic for plants or animals. Fungi include organisms in both the mold and yeast morphologies. Examples of vertebrates include fish and mammals, including cattle, goat, pig, sheep, hamster, mouse, rate and human; invertebrate animals include nematodes, insects, arachnids, and other arthropods. Preferably, the cell is a vertebrate cell. More preferably, the cell is a mammalian cell.

The cell having the target gene may be from the germ line or somatic, totipotent or pluripotent, dividing or non-dividing, parenchyma or epithelium, immortalized or transformed, or the like. The cell can be a gamete or an embryo; if an embryo, it can be a single cell embryo or a constituent cell or cells from a multicellular embryo. The term "embryo" thus encompasses fetal tissue. The cell having the target gene may be an undifferentiated cell, such as a stem cell, or a differentiated cell, such as from a cell of an organ or tissue, including fetal tissue, or any other cell present in an organism. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells, of the endocrine or exocrine glands.

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a small, interfering RNA or a template construct encoding such an RNA has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to, blood (e.g., hematopoietic cells (such as human hematopoietic progenitor cells, human hematopoietic stem cells, $CD34^+$ cells $CD4^+$ cells), lymphocytes and other blood lineage cells), bone marrow, brain, stem cells, blood vessel, liver, lung, bone, breast, cartilage, cervix, colon, cornea, embryonic, endometrium, endothelial, epithelial, esophagus, facia, fibroblast, follicular, ganglion cells, glial cells, goblet cells, kidney, lymph node, muscle, neuron, ovaries, pancreas, peripheral blood, prostate, skin, skin, small intestine, spleen, stomach, testes.

In certain embodiments, the host cell or tissue may be comprised in at least one organism. In certain embodiments, the organism may be, human, primate or murine. In other embodiments the organism may be any eukaryote or even a prokayrote (e.g., a eubacteria, an archaea), as would be understood by one of ordinary skill in the art (see, for example, webpage http://phylogeny.arizona.edu/tree/phylogeny.html). One of skill in the art would further understand the conditions under which to incubate all of the above described host cells to maintain them and to permit their division to form progeny.

6. Labels and Tags dsRNA or resulting siRNA may be labeled with a radioactive, enzymatic, colorimetric, or other label or tag for detection or isolation purposes. Nucleic acids may be labeled with fluorescence in some embodiments of the invention. The fluorescent labels contemplated for use as conjugates include, but are not limited to, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, TET, Tetramethylrhodamine, and/or Texas Red.

It is contemplated that dsRNA may be labeled with two different labels. Furthermore, fluorescence resonance energy transfer (FRET) may be employed in methods of the invention (e.g., Klostermeier et al., 2002; Emptage, 2001; Didenko, 2001, each incorporated by reference).

A number of techniques for visualizing or detecting labeled dsRNA are readily available. The reference by Stanley T. Crooke, 2000 has a discussion of such techniques (Chapter 6) which is incorporated by reference. Such techniques include, microscopy, arrays, Fluorometry, Light cyclers or other real time PCR machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al., 1997, spectroscopy, capillary gel electrophoresis (Cummins et al., 1996), spectroscopy; mass spectroscopy; radiological techniques; and mass balance techniques. Alternatively, nucleic acids may be labeled or tagged to allow for their efficient isolation. In other embodiments of the invention, nucleic acids are biotinylated.

7. Libraries and Arrays

The present methods and kits may be employed for high volume screening. A library of either dsRNA or candidate siRNA can be created using methods of the invention. This library may then be used in high throughput assays, including microarrays. Specifically contemplated by the present inventors are chip-based nucleic acid technologies such as those described by Hacia et al. (1996) and Shoemaker et al. (1996). Briefly, these techniques involve quantitative methods for analyzing large numbers of genes rapidly and accurately. By using fixed probe arrays, one can employ chip technology to segregate target molecules as high density arrays and screen these molecules on the basis of hybridization (see also, Pease et al., 1994; and Fodor et al, 1991). The term "array" as used herein refers to a systematic arrangement of nucleic acid. For example, a nucleic acid population that is representative of a desired source (e.g., human adult brain) is divided up into the minimum number of pools in which a desired screening procedure can be utilized to detect or deplete a target gene and which can be distributed into a single multi-well plate. Arrays may be of an aqueous suspension of a nucleic acid population obtainable from a desired mRNA source, comprising: a multi-well plate containing a plurality of individual wells, each individual well containing an aqueous suspension of a different content of a nucleic acid population. Examples of arrays, their uses, and implementation of them can be found in U.S. Pat. Nos. 6,329,209, 6,329,140, 6,324,479, 6,322,971, 6,316,193, 6,309,823, 5,412,087, 5,445,934, and 5,744,305, which are herein incorporated by reference.

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

The nucleic acid or analogue are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995a. See also DeRisi et al., 1996; Shalon et al., 1996; Schena et al., 1995b. Other methods for making microarrays, e.g., by masking (Maskos et al., 1992), may also be used. In principal, any type of array, for example, dot blots on a nylon hybridization membrane (see Sambrook et al., 1989, which is incorporated in its entirety for all purposes), could be used, although, as will be recognized by those of skill in the art, very small arrays will be preferred because hybridization volumes will be smaller.

II. Pharmaceutical Compositions And Routes Of Administration

Certain aspects of the present invention include compositions and methods of treating reducing or preventing the expression of a target gene in a cell by RNA interference. In non-limiting embodiments, the method can include obtaining at least one siRNA of 5, 6, 7, 8, 9, 10, 11, 12, 13, 14, 15, 16, 17, 18, 19, or 20 nucleotides in length and delivering the siRNA into a cell. The siRNA can be formulated into a pharmaceutical composition. An effective amount of the pharmaceutical composition can include, for example, an amount sufficient to detectably and repeatedly to ameliorate, reduce, minimize or limit the extent of the disease or its symptoms. More rigorous definitions may apply, including elimination, eradication or cure of disease.

1. Pharmaceutical Compositions

Pharmaceutical compositions of the present invention include siRNAs. The phrases "pharmaceutical or pharmacologically acceptable" refers to molecular entities and compositions that do not produce an adverse, allergic or other untoward reaction when administered to an animal, such as, for example, a human. The preparation of a pharmaceutical composition that includes an siRNA is known to those of skill in the art in light of the present disclosure, and as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

"Therapeutically effective amounts" are those amounts effective to produce beneficial results in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

A "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alternatively, a patient may be given $1\times10^{-5}$, $10^{-6}$, $10^{-6}$, $10^{-7}$, $10^{-8}$, $10^{-9}$, $10^{-10}$, $10^{-11}$, $10^{-12}$ M of a substance (or any range derivable therein), such as an siRNA, in a volume of 0.1 µl, 1.0 µl, 10 µl, 100 µl, 1 ml, 5 ml, 10 ml, 20 ml, 25 ml, 50 ml, 100 ml, 200 ml, 300 ml, 400 ml, 500 ml, or more (or any range derivable therein). siRNAs may be administered 1, 2, 3, 4, 5, 6, 7, 8, 9, 10 or more times over a course of 1, 2, 3, 4, 5, 6, 7, 8, 9 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, or 1, 2, 3, 4, 5, 6, 7, 8, 9, 10 or more years on a regular or as needed basis.

The compositions of the present invention may comprise different types of carriers depending on whether it is to be administered in solid, liquid or aerosol form, and whether it need to be sterile for such routes of administration as injection. The compositions may be formulated into a composition in a free base, neutral or salt form. In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. Sterile injectable solutions are prepared by incorporating the active compounds in the required amount in the appropriate solvent with various of the other ingredients enumerated above, as required, followed by filtered sterilization.

2. Routes of Administration

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrauterinely, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990).

III. Kits

Any of the compositions described herein may be comprised in a kit. In a non-limiting example, reagents for generating siRNA molecules are included in a kit. The kit may further include reagents for creating or synthesizing the dsRNA. It may also include one or more buffers, such as a nuclease buffer, transcription buffer, or a hybridization buffer, compounds for preparing the DNA template or the dsRNA, and components for isolating the resultant template, dsRNA, or siRNA. Other kits of the invention may include components for making a nucleic acid array comprising siRNA, and thus, may include, for example, a solid support.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 µg or at least or at most those amounts of dried dye are provided in kits of the invention. The dye may then be resuspended in any suitable solvent, such as DMSO.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Such kits may also include components that facilitate isolation of the DNA template, long dsRNA, or siRNA. It may also include components that preserve or maintain the nucleic acids or that protect against their degradation. Such components may be RNAse-free or protect against RNAses, such as RNase inhibitors. Such kits generally will comprise, in suitable means, distinct containers for each individual reagent or solution.

A kit can include instructions for employing the kit components as well the use of any other reagent not included in the kit. Instructions may include variations that can be implemented.

It is contemplated that such reagents are embodiments of kits of the invention. Such kits, however, are not limited to the particular items identified above and may include any labeling reagent or reagent that promotes or facilitates the labeling of a nucleic acid to trigger RNAi.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Transfection of GFP siRNAs or a negative control siRNA: Transfection was performed in adherent HeLa cells expressing GFP on glass cover slips in a 24 well dish using siPORT Lipid Reagent. At approximately 24 hours prior to transfection, Hela cells were plated into a 24-well dish at an appropriate density ~$5 \times 10^4$ cells/well in their normal growth media, DMEM/10% FBS. The cells were incubated at 37° C. overnight in humidified 5% $CO_2$ incubator.

Formation of a reagent/siRNA complex was performed in a sterile polystyrene 12×75 mm tubes. Dilute 2 ul of siPORT Lipid Reagent was added dropwise into 5.5 ul Opti-MEM® I complexing medium for a 7.5 ul final volume. The final volume was subsequently vortexed thoroughly and then left alone at room temperature for 10 min.

In each well, dilute 1.25 ul of (20 uM) of chemically synthesized siRNAs was added into 40 ul Opti-MEM® I media. Subsequently, diluted siRNAs was added to diluted siPORT Lipid Reagent, mix by gentle pipetting. Incubation occurred at room temperature for 20 min.

Cell preparation occurred by washing the cells with Opti-MEM® I, then adjusting the volume of media in each well containing cells to the pre-transfection volume of 200 μl (Opti-MEM® I). The reagent/siRNA complex was then added dropwise onto the cells. Without swirling, the dish was rocked back and forth to evenly distribute the complexes. Incubation occurred for 4 hours at 37° C. in humidified 5% $CO_2$ incubator. Subsequently, 500 ul fresh growth medium containing 1.5 times the normal concentration of serum was added to each well.

Assays were performed 48 h post transfection by analyzing GFP fluorescent signal using a fluorescent microscope.

Transfection of GAPDH siRNAs or a negative control siRNA: Transfection was performed into adherent HeLa cells in a 24 well dish using siPORT Lipid Reagent. At approximately 24 hours prior to transfection, Hela cells were plated into a 24-well dish at an appropriate density ~$5 \times 10^4$ cells/well in their normal growth media, DMEM/10% FBS. Incubation of the cells occurred at 37° C. overnight in humidified 5% $CO_2$ incubator.

Formation of the reagent/siRNA complex occurred in sterile polystyrene 12×75 mm tubes. Dilute 2 ul of siPORT Lipid Reagent was added dropwise into 5.5 ul Opti-MEM® I complexing medium for a 7.5 ul final volume. The final volume was vortexed thoroughly, and left to sit at room temperature for 10 min. For each well, dilute 1.25 ul of (20 uM) chemically synthesized siRNAs was placed into 40 ul Opti-MEM® I media. Diluted siRNAs were added to diluted siPORT Lipid Reagent, mix by gentle pipetting. Incubation occurred at room temperature for 20 min.

Cell preparation occurred by washing the cells with Opti-MEM® I, and then adjusting the volume of media in each well containing cells to the pre-transfection volume of 200 μl (Opti-MEM® I). Reagent/siRNA complex was added dropwise onto the cells by gently rocking the dish back and forth to evenly distribute the complexes. Incubation occurred for 4 hours at 37° C. in a humidified 5% $CO_2$ incubator. Subsequently, 500 ul fresh growth medium containing 1.5 times the normal concentration of serum was added to each well.

Assays were performed 48 h post transfection by analyzing GAPDH gene knockdown using western blot analysis and real time PCR.

Real time and western analysis: Samples were harvested 72 hours after transfection and were subjected to RNA and protein isolation using the PARIS™ Kit. To analyze RNA expression, RNA was reverse transcribed using the RETROscript® Kit, and target cDNA levels were analyzed by real-time PCR using SYBR® Green detection with primers specific to GAPDH. Target gene expression in the transfected cells was compared to cells transfected with an equal concentration of the Silencer Negative Control #1 siRNA. Input cDNA in the different samples was normalized using real-time PCR data for 18S rRNA. The bar graphs (FIG. 2A) represent an average of three data points.

Protocol for Western blot with Anti-GAPDH: Total protein concentration was determined using Bio-Rad Protein Assay Reagent (Cat #500-0006). Protein was loaded onto an acrylamide stacking gel-containing SDS. Mini Protein III system from Bio-Rad can be used. The gel was run at 200V until protein migrated approximately ⅔ of the gel distance. The protein was transferred at 300 mA to nitrocellulose membrane using the mini Protein III transfer apparatus. To block non-specific binding, the membrane was immersed in blocking reagent (1% Dry Milk in 1×PBS) for 1 hr at room temperature with rocking. The membrane was subsequently washed with 50 ml of PBST for 3×5 min. The Anti-GAPDH antibody was diluted in fresh blocking reagent and add 25 ml final volume to the membrane. GAPDH was used at 1 μg/ml final. The diluted GAPDH antibody can be reused for up to 3 times. The membrane was then incubated with the diluted primary antibody for 1 hr at room temperature with rocking. Subsequently, the membrane was washed with 50 ml of PBST (0.1% Tween-20 in 1×PBS) for 3×5 min. The secondary antibody (Peroxidase conjugated rabbit anti-mouse IgG, Sigma, Cat #A-9917) was diluted in fresh blocking reagent. The membrane was subsequently incubated with the diluted secondary antibody for 60 min at room temperature with rocking. The membrane was then washed with 50 ml of PBST for 3×5 min. Detection was performed by using ECL Detection Kits.

Example 2

Chemically Synthesized siRNAs Smaller than 21 by Mediate RNAi

Figure 1B:
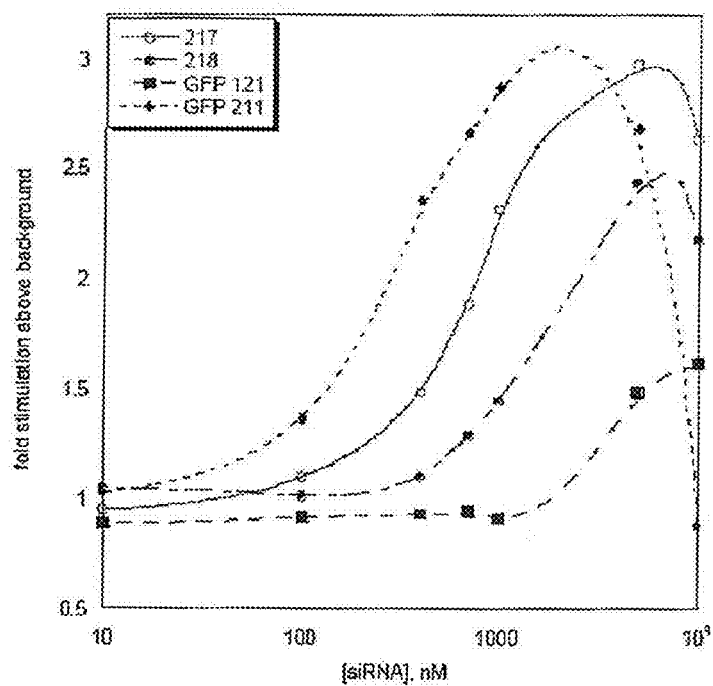

The inventors designed 12, 15, 17, 18, and 21 base siRNA and tested their potency in silencing GFP (FIG. 1A-FIG. 1B). The inventors synthesized these siRNA's by techniques that are known in the art and discussed throughout the specification. Table 1 includes the nucleic acid sequences of these molecules.

TABLE 1

| Nucleic Acid Sequence* | | SEQ ID NO. |
|---|---|---|
| GFP 12 | | |
| s  5' CAGGAACGCATT 3' | | 1 and 2 |
| as 5' TGCGUUCCUGUA 3' | | |
| GFP 15 | | |
| s  5' GUACAGGAACGCATT 3' | | 3 and 4 |
| as 5' UGCGUUCCTGUACAU 3' | | |
| GFP 17 | | |
| s  5' AUGUACAGGAACGCATT 3' | | 5 and 6 |
| as 5' UGCGUUCCUGUACAUAA 3' | | |
| GFP 18 | | |
| s  5' UAUGUACAGGAACGCATT 3' | | 7 and 8 |
| as 5' UGCGUUCCUGUACAUAAC 3' | | |

TABLE 1-continued

| Nucleic Acid Sequence* | SEQ ID NO. |
|---|---|
| GFP 21<br>s  5' GGUUAUGUACAGGAACGCAUU 3'<br>as 5' UGCGUUCCUGUACAUAACCUU 3' | 9 and 10 |

*"s" is sense and "as" is antisense.

These siRNAs were able to knock down the expression of their target gene (FIG. 1A-FIG. 1B). HeLa cells expressing GFP were transfected with the indicated siRNA and analyzed for the reduction in GFP levels using fluorescent microscope and image analysis software. The inventors also analyzed the effects that these siRNAs had on PKR activity. In vitro, the 21 base siRNA induced PKR more than the smaller siRNA sequences suggesting that shorter dsRNA may cause fewer off-target effects.

Example 3

Chemically Synthesized siRNAs can Silence an Endogenous Gene

Figure 2A:
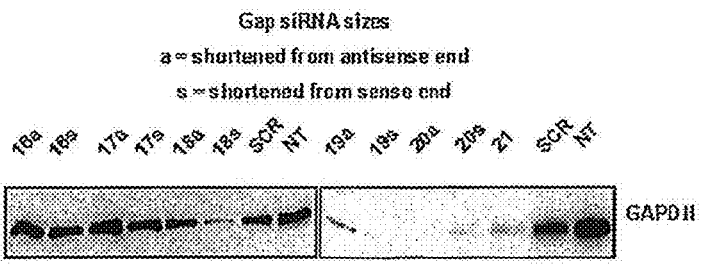
FIG. 2A-FIG. 2B. Smaller siRNA can knock down endogenous gene expression as determined by western and real time PCR analysis.
Figure 2B:
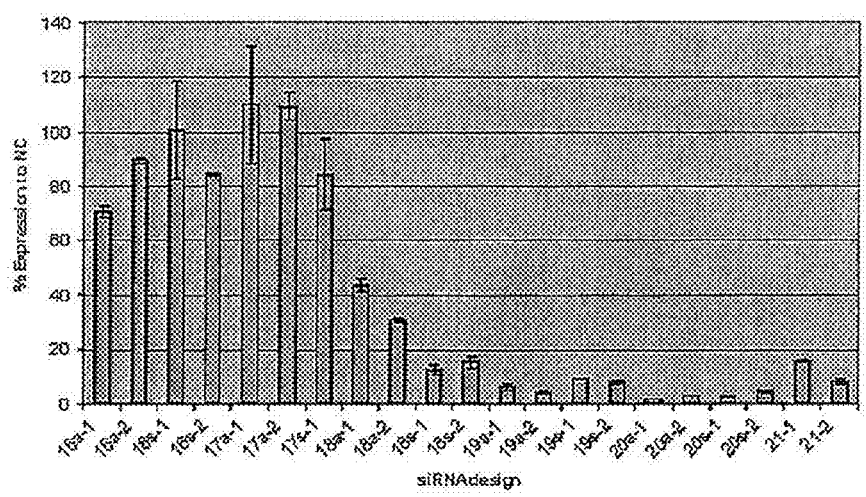

Smaller siRNA molecules targeting GAPDH were also tested to determine if an endogenous gene could be silenced. FIG. 2A-FIG. 2B include data that demonstrates that siRNA smaller than 21 base pairs can knock down endogenous gene expression. These data were obtained by western and real time PCR analysis. The nucleic acid sequences of these smaller siRNAs are listed in Table 2. The inventors synthesized these siRNA's by techniques that are known in the art and discussed throughout the specification.

TABLE 2

| Nucleic Acid Sequence* | SEQ ID NO. | % GC | Last 4 bp % GC 5' (as) | Last 4 bp % GC 5' (s) |
|---|---|---|---|---|
| GAP80 21<br>s  5' GUGGAUAUUGUUGCCAUCAUU 3'<br>as 3' UUCACCUAUAACAACGGUAGU 5' | 11 and 12 | $^{8}/_{21} = 38\%$ | $^{1}/_{4} = 25\%$ | $^{3}/_{4} = 75\%$ |

OFF FROM 5' END OF s STRAND

| Nucleic Acid Sequence* | SEQ ID NO. | % GC | Last 4 bp % GC 5' (as) | Last 4 bp % GC 5' (s) |
|---|---|---|---|---|
| GAP80-20<br>s  5' <u>U</u>GGAUAUUGUUGCCAUCAUU 3'<br>as 3' <u>U</u>CACCUAUAACAACGGUAGU 5' | 13 and 14 | $^{7}/_{20} = 35\%$ | $^{1}/_{4} = 25\%$ | $^{2}/_{4} = 50\%$ |
| GAP80-19<br>s  5' <u>G</u>GAUAUUGUUGCCAUCAUU 3'<br>as 3' <u>C</u>ACCUAUAACAACGGUAGU 5' | 15 and 16 | $^{7}/_{19} = 37\%$ | $^{1}/_{4} = 25\%$ | $^{2}/_{4} = 50\%$ |
| GAP80-18<br>s  5' <u>G</u>AUAUUGUUGCCAUCAUU 3'<br>as 3' <u>A</u>CCUAUAACAACGGUAGU 5' | 17 and 18 | $^{6}/_{18} = 33\%$ | $^{1}/_{4} = 25\%$ | $^{1}/_{4} = 25\%$ |
| GAP80-17<br>s  5' <u>A</u>UAUUGUUGCCAUCAUU 3'<br>as 3' <u>C</u>CUAUAACAACGGUAGU 5' | 19 and 20 | $^{5}/_{17} = 29\%$ | $^{1}/_{4} = 25\%$ | $^{0}/_{4} = 0\%$ |
| GAP80-16<br>s  5' <u>U</u>AUUGUUGCCAUCAUU 3'<br>as 3' <u>C</u>UAUAACAACGGUAGU 5' | 21 and 22 | $^{5}/_{16} = 31\%$ | $^{1}/_{4} = 25\%$ | $^{0}/_{4} = 0\%$ |

OFF FROM 5' END OF as STRAND

| Nucleic Acid Sequence* | SEQ ID NO. | % GC | Last 4 bp % GC 5' (as) | Last 4 bp % GC 5' (s) |
|---|---|---|---|---|
| GAP80-20<br>s  5' GUGGAUAUUGUUGCCAUC<u>U</u>U 3'<br>as 3' UUCACCAUAAACAACGGUA<u>G</u> 5' | 23 and 24 | $^{8}/_{20} = 40\%$ | $^{2}/_{4} = 50\%$ | $^{3}/_{4} = 75\%$ |
| Gap80-19<br>s  5' GUGGAUAUUGUUGCCAU<u>U</u>U 3'<br>   3' UUCACCUAUAACAACGGU<u>A</u> 5' | 25 and 26 | $^{7}/_{19} = 37\%$ | $^{2}/_{4} = 50\%$ | $^{3}/_{4} = 75\%$ |
| Gap80-18<br>s  5' GUGGAUAUUGUUGCC<u>A</u>UU 3'<br>as 3' UUCACCUAUAACAACGG<u>U</u> 5' | 27 and 28 | $^{7}/_{18} = 39\%$ | $^{3}/_{4} = 75\%$ | $^{3}/_{4} = 75\%$ |
| GAP80-17<br>s  5' GUGGAUAUUGUUGCC<u>U</u>U 3'<br>as 3' UUCACCUAUAACAACG<u>G</u> 5' | 29 and 30 | $^{7}/_{17} = 41\%$ | $^{3}/_{4} = 75\%$ | $^{3}/_{4} = 75\%$ |
| GAP80-16<br>s  5' GUGGAUAUUGUUGC<u>U</u>U 3'<br>as 3' UUCACCUAUAACAAC<u>G</u> 5' | 31 and 32 | $^{6}/_{16} = 38\%$ | $^{2}/_{4} = 50\%$ | $^{3}/_{4} = 75\%$ |

*"s" is sense and "as" is antisense.

Example 4

Chemically Synthesized siRNAs that are Smaller in Length to Cyclophilin

The inventors have also designed siRNAs that are smaller in length to cyclophilin. The inventors synthesized these siRNA's by techniques that are known in the art and discussed throughout the specification. These siRNAs are listed in Table 3 and are active against endogenous genes. The design of smaller siRNA against other genes using the procedures discussed throughout the specification is contemplated.

departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference.

TABLE 3

| Nucleic Acid Sequence* | SEQ ID NO. | % GC | Last 4 bp % GC 5' (as) | Last 4 bp % GC 5' (s) |
|---|---|---|---|---|
| Cyclo 175 21<br>s  5' AGGAUUUGGUUAUAAGGGUTT 3'<br>as 3' TTUCCUAAACCAAUAUUCCCA 5' | 33 and 34 | $^7/_{21}$ = 33% | $^3/_4$ = 75% | $^2/_4$ = 50% |
| *OFF FROM 5' END OF s STRAND* | | | | |
| Cyclo 175 20<br>s  5' GGAUUUGGUUAUAAGGGUTT 3'<br>as 3' TTCCUAAACCAAUAUUCCCA 5' | 35 and 36 | $^7/_{20}$ = 35% | $^3/_4$ = 75% | $^2/_4$ = 50% |
| Cyclo 175 19<br>s  5' GAUUUGGUUAUAAGGGUTT 3'<br>as 3' TTCUAAACCAAUAUUCCCA 5' | 37 and 38 | $^6/_{19}$ = 32% | $^3/_4$ = 75% | $^1/_4$ = 25% |
| Cyclo 175 18<br>s  5' AUUUGGUUAUAAGGGUTT 3'<br>as 3' TTUAAACCAAUAUUCCCA 5' | 39 and 40 | $^5/_{18}$ = 28% | $^3/_4$ = 75% | $^0/_4$ = 0% |
| Cyclo 175 17<br>s  5' UUUGGUUAUAAGGGUTT 3'<br>as 3' TTAAACCAAUAUUCCCA 5' | 41 and 42 | $^5/_{17}$ = 29% | $^3/_4$ = 75% | $^1/_4$ = 25% |
| Cyclo 175 16<br>s  5' UUGGUUAUAAGGGUTT 3'<br>as 3' TTAACCAAUAUUCCCA 5' | 43 and 44 | $^5/_{16}$ = 31% | $^3/_4$ = 75% | $^2/_4$ = 50% |
| *OFF FROM 5' END OF as STRAND* | | | | |
| Cyclo 175 20<br>s  5' AGGAUUUGGUUAUAAGGGTT 3'<br>as 3' TTUCCUAAACCAAUAUUCCC 5' | 45 and 46 | $^7/_{20}$ = 35% | $^3/_4$ = 75% | $^2/_4$ = 50% |
| Cyclo 175 19<br>s  5' AGGAUUUGGUUAUAAGGTT 3'<br>as 3' TTUCCUAAACCAAUAUUCC 5' | 47 and 48 | $^6/_{19}$ = 32% | $^2/_4$ = 50% | $^2/_4$ = 50% |
| Cyclo 175 18<br>s  5' AGGAUUUGGUUAUAAGTT 3'<br>as 3' TTUCCUAAACCAAUAUUC 5' | 49 and 50 | $^5/_{18}$ = 28% | $^1/_4$ = 25% | $^2/_4$ = 50% |
| Cyclo 175 17<br>s  5' AGGAUUUGGUUAUAATT 3'<br>as 3' TTUCCUAAACCAAUAUU 5' | 51 and 52 | $^4/_{17}$ = 24% | $^0/_4$ = 0% | $^2/_4$ = 50% |
| Cyclo 175 16<br>s  5' AGGAUUUGGUUAUATT 3'<br>as 3' TTUCCUAAACCAAUAU 5' | 53 and 54 | $^4/_{16}$ = 25% | $^0/_4$ = 0% | $^2/_4$ = 50% |

"s" is sense and "as" is antisense.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without U.S. Prov. Appl. 60/353,332
U.S. Pat. No. RE 35,443
U.S. Pat. No. 4,554,101
U.S. Pat. No. 4,659,774
U.S. Pat. No. 4,682,195
U.S. Pat. No. 4,683,202
U.S. Pat. No. 4,684,611
U.S. Pat. No. 4,704,362

U.S. Pat. No. 4,704,362
U.S. Pat. No. 4,786,600
U.S. Pat. No. 4,800,159
U.S. Pat. No. 4,816,571
U.S. Pat. No. 4,883,750
U.S. Pat. No. 4,952,496
U.S. Pat. No. 4,952,500
U.S. Pat. No. 4,959,463
U.S. Pat. No. 5,026,645
U.S. Pat. No. 5,037,745
U.S. Pat. No. 5,102,802
U.S. Pat. No. 5,141,813
U.S. Pat. No. 5,214,136
U.S. Pat. No. 5,221,619
U.S. Pat. No. 5,223,618
U.S. Pat. No. 5,264,566
U.S. Pat. No. 5,302,523
U.S. Pat. No. 5,322,783
U.S. Pat. No. 5,378,825
U.S. Pat. No. 5,384,253
U.S. Pat. No. 5,428,148
U.S. Pat. No. 5,445,934
U.S. Pat. No. 5,446,137
U.S. Pat. No. 5,464,765
U.S. Pat. No. 5,466,786
U.S. Pat. No. 5,470,967
U.S. Pat. No. 5,480,980
U.S. Pat. No. 5,538,877
U.S. Pat. No. 5,538,880
U.S. Pat. No. 5,550,318
U.S. Pat. No. 5,554,744
U.S. Pat. No. 5,563,055
U.S. Pat. No. 5,574,146
U.S. Pat. No. 5,580,859
U.S. Pat. No. 5,583,013
U.S. Pat. No. 5,589,466
U.S. Pat. No. 5,591,601
U.S. Pat. No. 5,591,616
U.S. Pat. No. 5,602,240
U.S. Pat. No. 5,602,244
U.S. Pat. No. 5,610,042
U.S. Pat. No. 5,610,289
U.S. Pat. No. 5,614,617
U.S. Pat. No. 5,623,070
U.S. Pat. No. 5,637,683
U.S. Pat. No. 5,645,897
U.S. Pat. No. 5,652,099
U.S. Pat. No. 5,656,610
U.S. Pat. No. 5,670,663
U.S. Pat. No. 5,672,697
U.S. Pat. No. 5,681,947
U.S. Pat. No. 5,700,922
U.S. Pat. No. 5,702,932
U.S. Pat. No. 5,705,629
U.S. Pat. No. 5,708,154
U.S. Pat. No. 5,714,606
U.S. Pat. No. 5,728,525
U.S. Pat. No. 5,736,524
U.S. Pat. No. 5,744,305
U.S. Pat. No. 5,763,167
U.S. Pat. No. 5,777,092
U.S. Pat. No. 5,780,448
U.S. Pat. No. 5,789,215
U.S. Pat. No. 5,792,847
U.S. Pat. No. 5,795,715
U.S. Pat. No. 5,824,528
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,858,988
U.S. Pat. No. 5,859,221
U.S. Pat. No. 5,866,366
U.S. Pat. No. 5,869,320
U.S. Pat. No. 5,872,232
U.S. Pat. No. 5,882,864
U.S. Pat. No. 5,886,165
U.S. Pat. No. 5,891,681
U.S. Pat. No. 5,891,681
U.S. Pat. No. 5,912,148
U.S. Pat. No. 5,916,776
U.S. Pat. No. 5,916,779
U.S. Pat. No. 5,922,574
U.S. Pat. No. 5,928,905
U.S. Pat. No. 5,928,906
U.S. Pat. No. 5,932,451
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,624
U.S. Pat. No. 6,114,152
U.S. Pat. No. 6,251,666
U.S. Pat. No. 6,309,823
U.S. Pat. No. 6,316,193
U.S. Pat. No. 6,322,971
U.S. Pat. No. 6,324,479
U.S. Pat. No. 6,329,140
U.S. Pat. No. 6,329,209
PCT Applic. No. PCT/US87/00880
PCT Applic. No. PCT/US89/01025
PCT Applic. No. WO 00/44914
PCT Applic. No. WO 01/68836
PCT Applic. No. WO 01/36646
PCT Applic. No. WO 89/100700
PCT Applic. No. WO 99/32619
PCT Applic. No. WO 88/10315
PCT Applic. No. WO 94/09699
PCT Applic. No. WO 90/07641
PCT Applic. No. WO 95/06128
PCT Applic. No. WO 91/05,866
PCT Applic. No. WO 91/02,818
GB Application No. 2 202 328
European Appl. 0,178,863
European Appl. 266,032
European Appl. 266,032
European Appl. 320,308
European Appl. 329,822
Antisense Drug Technology, Stanley T. Crooke (ed), Marcel Dekker and Co, Basel, Switzerland, Chapter 6, 2001.
Ausubel et al., *In: Current Protocols in Molecular Biology*, John, Wiley and Sons, Inc, New York, 1994.
Baglioni and Nilson, *Interferon*, 5:23-42, 1983.
Beaucage and Lyer, *Tetrahedron*, 48:2223-2311, 1992.
Bernstein et al., *Nature*, 409: 363-366, 2001.
Blaszczyk et al., *Structure*, 9(12):1225-1236, 2001.
Bosher and Labouesse, *Nat. Cell Biol.*, 2:E31-E36, 2000.
Brown et al., *Ambion TechNotes* 9(1): 3-6, 2002.
Brummelkamp et al., *Science*, 296(5567):550-553, 2002.
Calegari et al., *Proc Natl Acad Sci USA*, 99(22):14236, 2002.

Caplen et al., *Proc Natl Acad Sci USA*, 98: 9742-9747, 2001.
Chen and Okayama, *Mol. Cell. Biol.*, 7(8):2745-2752, 1987.
Cogoni and Macino, *Science*, 286:342-2344, 1999.
Cogoni and Macino, *Nature*, 399:166-169, 1999.
Court, in "Control of Messenger RNA Stability" (J. G. Belarco and G. Brauerman, eds., Academic Press, New York) 1993.
Cummins et al., *In IRT: Nucleosides and nucleosides*, La Jolla Calif., 72, 1996.
Dalmay et al., *EMBO J.*, 20:2069-2078, 2001.
Dalmay et al., *Cell*, 101:543-553, 2000.
DeRisi et al., *Nature Genetics* 14:457-460, 1996.
Didenko, *Biotechniques*, 31(5):1106-16, 1118, 1120-1, 2001.
Dunn, in "The Enzymes" (P. D. Boyer, ed., Academic Press, New York) 1982.
Elbashir et al., *Genes Dev.* 15: 188-200, 2001.
Elbashir et al., *Nature*, 411:494-498, 2001.
Emptage et al., *Neuron*, 2001 January; 29(1):197-208, 2001.
Fechheimer et al., *Proc. Natl. Acad. Sci. USA*, 84:8463-8467, 1987.
Fire et al., *Nature*, 391:806-811, 1998.
Fodor et al., *Science*, 251:767-773, 1991.
Ford and Latham, *R&D Magazine*, pp. 48-50, July 2003.
Forster et al., *Nucleic Acids Res.*, 13(3):745-761, 1985.
Fraley et al., *Proc. Natl. Acad. Sci. USA*, 76:3348-3352, 1979.
Froehler et al., *Nucleic Acids Res.*, 14(13):5399-5407, 1986.
Frohman, In: *PCR Protocols: A Guide To Methods and Applications*, Academic Press, NY, 1990.
Gillam et al., *J. Biol. Chem.*, 253:2532, 1978.
Gillam et al., *Nucleic Acids Res.*, 6:2973, 1979.
Gopal, *Mol. Cell. Biol.*, 5:1188-1190, 1985.
Graham and Van Der Eb, *Virology*, 52:456-467, 1973.
Griffey et al., *J. Mass. Spectrom.*, 32(3):305-13, 1997.
Grishok et al., *Cell*, 106: 23-34, 2001.
Hacia et al., *Nature Genetics*, 14:441-447, 1996.
Hamilton and Baulcombe, *Science*, 286:950-952, 1999.
Hammond et al., *Nat. Rev. Genet.*, 2(2):110-9, 2001.
Harland and Weintraub, *J. Cell. Biol.*, 101:1094-1099, 1985.
Higgins et al., *Comput. Appl. Biosci.*, 8(2):189-191, 1992.
Hutvagner et al., *Science*, 293:834-838, 2001.
Innis et al., *Proc. Natl. Acad. Sci. USA*, 85(24):9436-9440, 1988.
Inouye and Inouye, *Nucleic Acids Res.*, 13:3101-3109, 1985.
Itakura and Riggs, *Science*, 209:1401-1405, 1980.
Itakura et al., *J. Biol. Chem.*, 250:4592 1975.
Jacque et al., *Nature*, 2002.
Johnson et al., In: *Biotechnology and Pharmacy*, Pezzuto et al., (eds), Chapman and Hall, New York, 1993.
Kaeppler et al., *Plant Cell Reports*, 9:415-418, 1990.
Kaneda et al., *Science*, 243:375-378, 1989.
Kato et al., *J. Biol. Chem.*, 266:3361-3364, 1991.
Ketting et al., *Cell*, 99:133-141, 1999.
Kharrat et al., *EMBO. J.*, 14(14):3572-3584, 1995.
Khorana, *Science*, 203, 614 1979.
Klostermeier and Millar, *Biopolymers*, 61(3):159-79, 2001-2002
Knight et al., *Science*, 2:2, 2001.
Kornberg and Baker, In: *DNA Replication*, 2nd Ed., Freeman, San Francisco, 1992.
Kwoh et al., *Proc. Natl. Acad. Sci. USA*, 86: 1173, 1989.
Kyte and Doolittle, *J. Mol. Biol.*, 157(1):105-132, 1982.
Lee et al., *DNA Cell Biol.*, 16(11):1267-1275, 1997.
Lin and Avery, *Nature*, 402:128-129, 1999.
Maskos et al., *Nuc. Acids. Res.* 20:1679-1684, 1992.
Miyagishi and Taira, *Biotechnol.*, 5:497-500, 2002.
Montgomery et al., *Proc. Natl. Acad. Sci. USA*, 95:155-2-15507, 1998.
Mourrain et al., *Cell*, 101:533, 2000.
Nicholson, *FEMS Microbiol. Rev.* 23: 371, 1999.
Nicolau and Sene, *Biochim. Biophys. Acta*, 721:185-190, 1982.
Nicolau et al., *Methods Enzymol.*, 149:157-176, 1987.
Nishikura, *Cell* 16:415-418, 2001.
Novina et al., *Nat. Med.*, 8:681-686, 2002.
Ohara et al., *Proc. Natl. Acad. Sci.* USA, 86:5673-5677, 1989.
Omirulleh et al., *Plant Mol. Biol.*, 21(3):415-428, 1993.
Paul et al., *Nat. Biotechnol.*, 20:505-508, 2002.
Pease et al., *Proc. Natl. Acad. Sci. USA*, 91:5022-5026, 1994.
Plasterk and Ketting, *Curr. Opin. Genet. Dev.*, 10:562-567, 2000.
Potrykus et al., *Mol. Gen. Genet.*, 199(2):169-77, 1985.
Rippe et al., *Mol. Cell. Biol.*, 10:689-695, 1990.
Robertson et al., *J. Biol. Chem.* 243: 82, 1968.
Saiki et al. *Science*, 230:1350-1354, 1985
Sambrook et al., In: *Molecular cloning*, Cold Spring Harbor Laboratory Press, Cold Spring Harbor, N.Y., 2001.
Scheit, In: *Synthesis and Biological Function*, Wiley-Interscience, NY, 171-172, 1980.
Schena et al., *Science* 270:467-470, 1995a.
Schena et al., *Proc. Natl. Acad. Sci. USA* 93:10539-11286, 1995b.
Shalon et al., *Genome Res.* 6:639-645, 1996.
Sharp and Zamore, *Science*, 287:2431-2433, 2000.
Sharp, *Genes Dev.*, 13:139-141, 1999.
Shoemaker et al., *Nature Genetics*, 14:450-456, 1996.
Smardon et al., *Curr. Biol.*, 10:169-178, 2000.
Sui et al., *Proc. Natl. Acad. Sci. USA*, 99(8):5515-5520, 2002.
Tabara et al., *Cell*, 99:123-132, 1999.
Thompson et al., *Nucleic Acids Res.*, 22(22):4673-4680, 1994.
Trotta et al., Cancer Cell 3:(2):145-60, 2003.
Tuschl, *Chembiochem.*, 2:239-245, 2001.
Walker et al., *Proc. Natl. Acad. Sci. USA*, 89:392-396 1992.
Waterhouse et al., *Nature*, 411:834-842, 2001.
Williams et al., *Int. J. Dev. Biol.*, 41(2):359-364, 1997.
Wong et al., *Gene*, 10:87-94, 1980.
Wu-Scharf et al., *Science*, 290:1159-1162, 2000.
Yang et al., *Proc. Natl. Acad. Sci. USA*, 99(15): 9942-7, 2002.
Yu et al., *Proc. Natl. Acad. Sci. USA*, 99:6047-6052, 2002.
Zamore et al., *Cell.* 101:25-33, 2000.
Zamore, *Nat. Struct. Biol.*, 8:746-750, 2001.

What is claimed is:

1. A composition comprising isolated dsRNA, wherein the isolated dsRNA comprises a nucleotide sequence selected from the group consisting of SEQ ID NO: 11, SEQ ID NO: 12, SEQ ID NO: 13; SEQ ID NO: 14, SEQ ID NO: 15, SEQ ID NO: 16, SEQ ID NO: 17; SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30; SEQ ID NO: 31, and SEQ ID NO: 32.

2. The composition of claim 1, wherein the dsRNA comprises a terminal 3' hydroxyl group.

3. The composition of claim 1, wherein the dsRNA is chemically synthesized dsRNA.

4. The composition of claim 1, wherein the dsRNA is formulated with a pharmaceutically acceptable composition.

5. The composition of claim 1, wherein the isolated dsRNA comprises SEQ ID NO:11.

6. The composition of claim 1, wherein the isolated dsRNA comprises SEQ ID NO:12.

7. The composition of claim 1, wherein the isolated dsRNA comprises SEQ ID NO:13.

8. The composition of claim 1, wherein the isolated dsRNA comprises SEQ ID NO:14.

9. The composition of claim 1, wherein the isolated dsRNA comprises SEQ ID NO:15.

10. The composition of claim 1, wherein the isolated dsRNA comprises SEQ ID NO:16.

11. The composition of claim 1, wherein the isolated dsRNA comprises SEQ ID NO:17.

12. The composition of claim 1, wherein the isolated dsRNA comprises SEQ ID NO:18.

13. The composition of claim 1, wherein the isolated dsRNA comprises SEQ ID NO:19.

14. The composition of claim 1, wherein the isolated dsRNA comprises SEQ ID NO:20.

15. The composition of claim 1, wherein the isolated dsRNA comprises SEQ ID NO:21.

16. The composition of claim 1, wherein the isolated dsRNA comprises SEQ ID NO:22.

17. The composition of claim 1, wherein the isolated dsRNA comprises SEQ ID NO:31.

18. The composition of claim 1, wherein the isolated dsRNA comprises SEQ ID NO:32.

19. A method of reducing expression of a target gene in a cell comprising:
 a) obtaining at least one siRNA of claim 1; and
 b) delivering the siRNA into the cell.

* * * * *

SEQUENCE LISTING

<160> NUMBER OF SEQ ID NOS: 54

<210> SEQ ID NO 1
<211> LENGTH: 12
<212> TYPE: DNA
<213> ORGANISM: Artificial Sequence -continued

```
<220> FEATURE:
<223> OTHER INFORMATION: Description of Artificial Sequence: Synthetic
      Primer

<400> SEQUENCE: 1
caggaacgca tt                                                            12

<210> SEQ ID NO 2
<211> LENGTH: 12
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 2
tgcguuccug ua                                                            12

<210> SEQ ID NO 3
<211> LENGTH: 15
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 3
guacaggaac gcatt                                                         15

<210> SEQ ID NO 4
<211> LENGTH: 15
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 4
ugcguucctg uacau                                                         15

<210> SEQ ID NO 5
<211> LENGTH: 17
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 5
auguacagga acgcatt                                                       17

<210> SEQ ID NO 6
<211> LENGTH: 17
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
```

```
<220> FEATURE:
<223> OTHER INFORMATION: Description of Artificial Sequence:  Synthetic
      Primer

<400> SEQUENCE: 6
ugcguuccug uacauaa                                                        17

<210> SEQ ID NO 7
<211> LENGTH: 18
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 7
uauguacagg aacgcatt                                                       18

<210> SEQ ID NO 8
<211> LENGTH: 18
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 8
ugcguuccug uacauaac                                                       18

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 9
gguuauguac aggaacgcat t                                                   21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 10
ugcguuccug uacauaacct t                                                   21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
```

```
<220> FEATURE:
<223> OTHER INFORMATION: Description of Artificial Sequence:  Synthetic
      Primer

<400> SEQUENCE: 11
guggauauug uugccaucat t                                                   21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 12
ttcaccuaua acaacgguag u                                                   21

<210> SEQ ID NO 13
<211> LENGTH: 20
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 13
uggauauugu ugccaucatt                                                     20

<210> SEQ ID NO 14
<211> LENGTH: 20
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 14
ucaccuauaa caacgguagu                                                     20

<210> SEQ ID NO 15
<211> LENGTH: 19
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 15
ggauauuguu gccaucatt                                                      19

<210> SEQ ID NO 16
<211> LENGTH: 19
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
```

```
<220> FEATURE:
<223> OTHER INFORMATION: Description of Artificial Sequence: Synthetic
      Primer

<400> SEQUENCE: 16
caccuauaac aacgguagu                                                   19

<210> SEQ ID NO 17
<211> LENGTH: 18
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 17
gauauuguug ccaucatt                                                    18

<210> SEQ ID NO 18
<211> LENGTH: 18
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 18
accuauaaca acgguagu                                                    18

<210> SEQ ID NO 19
<211> LENGTH: 17
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 19
auauuguugc caucatt                                                     17

<210> SEQ ID NO 20
<211> LENGTH: 17
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 20
ccuauaacaa cgguagu                                                     17

<210> SEQ ID NO 21
<211> LENGTH: 16
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
```

```
<220> FEATURE:
<223> OTHER INFORMATION: Description of Artificial Sequence:  Synthetic
      Primer

<400> SEQUENCE: 21
uauuguugcc aucatt                                                        16

<210> SEQ ID NO 22
<211> LENGTH: 16
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 22
cuauaacaac gguagu                                                        16

<210> SEQ ID NO 23
<211> LENGTH: 20
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 23
guggauauug uugccauctt                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 24
ttcaccuaua acaacgguag                                                    20

<210> SEQ ID NO 25
<211> LENGTH: 19
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 25
guggauauug uugccautt                                                     19

<210> SEQ ID NO 26
<211> LENGTH: 19
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
```

```
<220> FEATURE:
<223> OTHER INFORMATION: Description of Artificial Sequence:  Synthetic
      Primer

<400> SEQUENCE: 26
ttcaccuaua acaacggua                                                      19

<210> SEQ ID NO 27
<211> LENGTH: 18
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 27
guggauauug uugccatt                                                       18

<210> SEQ ID NO 28
<211> LENGTH: 18
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 28
ttcaccuaua acaacggu                                                       18

<210> SEQ ID NO 29
<211> LENGTH: 17
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 29
guggauauug uugcctt                                                        17

<210> SEQ ID NO 30
<211> LENGTH: 17
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 30
ttcaccuaua acaacgg                                                        17

<210> SEQ ID NO 31
<211> LENGTH: 16
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
```

```
<220> FEATURE:
<223> OTHER INFORMATION: Description of Artificial Sequence:  Synthetic
      Primer

<400> SEQUENCE: 31
guggauauug uugctt                                                           16

<210> SEQ ID NO 32
<211> LENGTH: 16
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 32
ttcaccuaua acaacg                                                           16

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 33
aggauuuggu uauaagggut t                                                     21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 34 ttccuaaac caauauuccc a                                                      21

<210> SEQ ID NO 35
<211> LENGTH: 20
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 35
ggauuugguu auaagggutt                                                       20

<210> SEQ ID NO 36
<211> LENGTH: 20
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
```

-continued

```
<220> FEATURE:
<223> OTHER INFORMATION: Description of Artificial Sequence:  Synthetic
      Primer

<400> SEQUENCE: 36
ttccuaaacc aauauuccca                                                    20

<210> SEQ ID NO 37
<211> LENGTH: 19
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 37
gauuugguua uaagggutt                                                     19

<210> SEQ ID NO 38
<211> LENGTH: 19
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 38
ttcuaaacca auauuccca                                                     19

<210> SEQ ID NO 39
<211> LENGTH: 18
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 39
auuugguuau aagggutt                                                      18

<210> SEQ ID NO 40
<211> LENGTH: 18
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 40
ttuaaaccaa uauuccca                                                      18

<210> SEQ ID NO 41
<211> LENGTH: 17
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
```

```
<220> FEATURE:
<223> OTHER INFORMATION: Description of Artificial Sequence: Synthetic
      Primer

<400> SEQUENCE: 41
uuugguuaua agggutt                                                        17

<210> SEQ ID NO 42
<211> LENGTH: 17
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 42
ttaaaccaau auuccca                                                        17

<210> SEQ ID NO 43
<211> LENGTH: 16
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 43
uugguuauaa gggutt                                                         16

<210> SEQ ID NO 44
<211> LENGTH: 16
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 44
ttaaccaaua uuccca                                                         16

<210> SEQ ID NO 45
<211> LENGTH: 20
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 45
aggauuuggu uauaagggtt                                                     20

<210> SEQ ID NO 46
<211> LENGTH: 20
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
```

```
<220> FEATURE:
<223> OTHER INFORMATION: Description of Artificial Sequence:  Synthetic
      Primer

<400> SEQUENCE: 46
ttuccuaaac caauauuccc                                                    20

<210> SEQ ID NO 47
<211> LENGTH: 19
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 47
aggauuuggu uauaaggtt                                                     19

<210> SEQ ID NO 48
<211> LENGTH: 19
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 48
ttuccuaaac caauauucc                                                     19

<210> SEQ ID NO 49
<211> LENGTH: 18
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 49
aggauuuggu uauaagtt                                                      18

<210> SEQ ID NO 50
<211> LENGTH: 18
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence:  Synthetic
      Primer

<400> SEQUENCE: 50
ttuccuaaac caauauuc                                                      18

<210> SEQ ID NO 51
<211> LENGTH: 17
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
```

```
<220> FEATURE:
<223> OTHER INFORMATION: Description of Artificial Sequence: Synthetic
      Primer

<400> SEQUENCE: 51
aggauuuggu uauaatt                                                    17

<210> SEQ ID NO 52
<211> LENGTH: 17
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 52
ttuccuaaac caauauu                                                    17

<210> SEQ ID NO 53
<211> LENGTH: 16
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 53
aggauuuggu uauatt                                                     16

<210> SEQ ID NO 54
<211> LENGTH: 16
<212> TYPE: DNA
<213> ORGANISM: Artificial Sequence
<220> FEATURE:
<223> OTHER INFORMATION: Description of Combined DNA/RNA Molecule:
      Isolated RNA comprising a nucleotide sequence
<220> FEATURE:
<223> OTHER INFORMATION: Description of Artificial Sequence: Synthetic
      Primer

<400> SEQUENCE: 54
ttuccuaaac caauau                                                     16
```